United States Patent
Otvos

(10) Patent No.: US 9,435,870 B2
(45) Date of Patent: Sep. 6, 2016

(54) METHODS, SYSTEMS AND COMPUTER PROGRAMS FOR ASSESSING CHD RISK USING ADJUSTED HDL PARTICLE NUMBER MEASUREMENTS

(75) Inventor: James D. Otvos, Apex, NC (US)

(73) Assignee: LIPOSCIENCE, INC., Raleigh, NC (US)

( * ) Notice: Subject to any disclaimer, the term of this patent is extended or adjusted under 35 U.S.C. 154(b) by 1423 days.

(21) Appl. No.: 11/746,812

(22) Filed: May 10, 2007

(65) Prior Publication Data

US 2007/0264677 A1 Nov. 15, 2007

Related U.S. Application Data

(60) Provisional application No. 60/746,894, filed on May 10, 2006.

(51) Int. Cl.
| | | |
|---|---|---|
| G01N 33/48 | (2006.01) |
| G01N 33/50 | (2006.01) |
| G01R 33/465 | (2006.01) |
| G06F 19/00 | (2011.01) |
| G06F 19/12 | (2011.01) |
| G06F 19/24 | (2011.01) |
| G01N 24/08 | (2006.01) |

(52) U.S. Cl.
CPC .............. *G01R 33/465* (2013.01); *G01N 24/08* (2013.01); *G06F 19/12* (2013.01); *G06F 19/24* (2013.01); *G06F 19/34* (2013.01); *G06F 19/345* (2013.01); *G06F 19/3431* (2013.01); *G06F 19/3437* (2013.01); *G01N 2800/323* (2013.01); *G01N 2800/324* (2013.01)

(58) Field of Classification Search
None
See application file for complete search history.

(56) References Cited

U.S. PATENT DOCUMENTS

| | | |
|---|---|---|
| 4,933,844 A | 6/1990 | Otvos |
| 5,343,389 A | 8/1994 | Otvos |
| 6,576,471 B2 | 6/2003 | Otvos |
| 6,617,167 B2 | 9/2003 | Otvos et al. |
| 7,491,543 B2 | 2/2009 | Barzilai |

(Continued)

FOREIGN PATENT DOCUMENTS

| | | |
|---|---|---|
| EP | 0361214 | 4/1990 |
| WO | WO93/03450 | 2/1993 |

(Continued)

OTHER PUBLICATIONS

Soedamah-Muthu et al. The effect of atorvastin on serum lipids, lipoproteins and NMR spectroscopy defined lipoprotein subclasses in type 2 diabetic patients with ischaemic heart disease. Atherosclerosis, vol. 167, 2003, pp. 243-255.*

(Continued)

*Primary Examiner* — Russell S Negin
(74) *Attorney, Agent, or Firm* — Kilpatrick Townsend & Stockton LLP

(57) ABSTRACT

Methods, computer program products and apparatus determine a subject's risk of having or developing CHD using a calculated HDL particle risk number and/or a mathematical model of risk associated with HDL particles that adjusts concentrations of at least one of the subclasses of small, medium and large HDL particle measurements to reflect predicted CHD risk. A calculated LDL particle risk number may also be generated as well as a lipoprotein particle index derived from the ratio of $R_{LDL}/R_{HDL}$.

33 Claims, 9 Drawing Sheets

(56) References Cited

U.S. PATENT DOCUMENTS

| | | | |
|---|---|---|---|
| 7,790,465 B2* | 9/2010 | Otvos | 436/71 |
| 8,420,337 B2 | 4/2013 | Heinecke et al. | |
| 2001/0004732 A1* | 6/2001 | Satoh | 705/2 |
| 2006/0183234 A1 | 8/2006 | Otvos | |

FOREIGN PATENT DOCUMENTS

| | | |
|---|---|---|
| WO | WO00/05154 | 8/2000 |
| WO | WO2005/043171 A1 | 5/2005 |
| WO | WO2005/119285 A1 | 12/2005 |

OTHER PUBLICATIONS

Manninen et al. Joint effects of serum triglyceride and LDL cholesterol and HDL cholesterol concentrations on coronary heart disease risk in the Helsinki Heart Study. Circulation, vol. 85, 1992, pp. 37-45.*

Delaglio et al. Measurement of homonuclear proton couplings from regular 2D COSY spectra. Journal of Magnetic Resonance, 2001, vol. 149, pp. 276-281.*

International Search Report and Written Opinion for International Application No. PCT/US2007/011229, International filing date Sep. 5, 2007, Date of mailing Apr. 17, 2008.

Atger et al., High-Density Lipoprotein Subfractions as Markers of Early Atherosclerosis, American Journal of Cardiology, Cahners Publishing Co., 1995, pp. 127-131, vol. 75, No. 2.

Grundy et al., Assessment of Cardiovascular Risk by Use of Multiple-Risk-Factor Assessment Equations: A Statement for Healthcare Professionals From the American Heart Association and the American College of Cartiology, Circulation, 1999,.pp. 1481-1492, vol. 100.

Cromwell et al.; "Low-density lipoprotein particle number and risk for cardiovascular disease" *Curr. Atheroscler. Rep.* 6 381-387 (2004).

Campos et al.; "Predominance of large LDL and reduced HDL2 cholesterol in normolipidemic men with coronary heart disease" *Arterioscler Thromb Vasc Biol* 15 1043-1048 (1995).

Campos et al.; "Low-density lipoprotein size, pravastatin treatment, and coronary events" *JAMA* 2861468-1474 (2001).

Dreon et al.; "Change in dietary saturated fat intake is correlated with change in mass of large low-density-lipoprotein particles in men" *Am. J. Clin. Nutr.* 67 828-836 (1998).

Grundy , S.M. et al.; "Hepatic lipase influences high density lipoprotein subclass distribution in normotriglyceridemic men: genetic and pharmacological evidence" *J. Lipid Res.* 40 229-234 (1999).

Hildebrand, F.B.; *Introduction to Numerical Analysis*, $2^{nd}$ edition 314-326, 539-567, McGraw-Hill (1975).

McNamara Jr., et al.; "Differences in LDL subspecies involve alterations in lipid composition and conformational changes in apolipoprotein B" *J. Lipid Res.* 37 1924-1935 (1996).

Mora et al.; "Both Large and Small LDL Particle concentrations are Independently Associated with Carotid Atherosclerosis in the Multi-Ethnic Study of Atherosclerosis (MESA)" 2005 Scientific Sessions of the American Heart Association, Dallas, Texas *Circulation* 112 II-802 (2005). Abstract only.

Mora et al.; "LDL particle subclasses, LDL particle size, and carotid atherosclerosis in the Multi-Ethnic Study of Atherosclerosis (MESA)" *Atherosclerosis* [*online pre-print publication*] 7 pages (2006).

O'Leary et al.; "Intima-media thickness; a tool for atherosclerosis imaging and event prediction" *Am. J. Cardiol.* 90 18L-21L (2002).

Otvos, J.D. et al.; "Development of a proton nuclear magnetic resonance spectroscopic method for determining plasma lipoprotein concentrations and subspecies distributions from a single, rapid measurement" *Clin. Chem.* 38 1632-1638 (1992).

Otvos, J.D. et al.; "Measurement of lipoprotein subclass profiles by nuclear magnetic resonance spectroscopy" *Clin. Lab.* 48 171-180 (2002).

Otvos et al.; "Low-Density Lipoprotein and High-Density Lipoprotein Particle Subclasses Predict Coronary Events and Are Favorably Changed by Gemfibrozil Therapy in the Veterans Affairs High-Density Lipoprotein Intervention Trial" *Circulation* 113 1556-1563 (2006).

Patsch et al.; "Characterization of lipoprotein in a kindred with familial hypercholesterolemia" *J. Lipid Res.* 23 1196-1205 (1982).

Redgrave, TG et al.; "Changes in plasma very low density and low density lipoprotein content, composition, and size after a fatty meal in normo- and hypertriglyceridemic man" *J. Lipid Res.* 20 217-29 (1979).

Rifai, N. et al.; *Handbook of LipoProtein Testing*, $2^{nd}$ Edition, Washington, DC, AACC Press; 2000, 609-623.

Rosenson et al.; Relations of lipoprotein subclass levels and low density lipoprotein size to progression of coronary artery disease in the Pravastatin Limitation of Atherosclerosis in the Coronary Arteries (PLAC-1) trial *Am. J. Cardio.* 90 89-94 (2002).

Rumsey et al.; "Cryopreservation with sucrose maintains normal physical and bioloOgical properties of human plasma low density lipoproteins" *J. Lipid. Res.* 33 1551-1561 (1992).

Sacks et al.; "Clinical review 163: Cardiovascular endocrinology: Low density lipoprotein size and cardiovascular disease: a reappraisal" *J. Clin. Endocrinol Metab.* 88 4525-4532 (2003).

Wilson et al.; "Impact of National Guidelines for Cholesterol Risk Factor Screening" *JAMA* 262:1 41-44 (1989).

Garvey et al., "Effects of Insulin Resistance and Type 2 Diabetes on Lipoprotein Subclass Particle Size and Concentration Determined by Nuclear Magnetic Resonance" Diabetes Feb. 2003, 52: 453-462.

Pascot et al., "Reduced HDL Particle Size as an Additional Feature of the Atherogenic Dyslipdemia of Abdominal Obesity" Journal of Lipid Research 2001, 42: 2007-2014.

Syvanne et al,, "High Density Lipoprotein Subfractions in Non-insulin Dependent Diabetes mellitus and Coronary Artery Disease" Journal of Lipid Research 1995, 36: 573-582.

\* cited by examiner

| PATIENT NAME | SEX | AGE | | CLINICIAN | |
|---|---|---|---|---|---|
| | | | | | |

| PATIENT ID | BIRTH DATE | ACCESSION # | CLIENT NAME AND ADDRESS |
|---|---|---|---|
| | | | |

| DATE COLLECTED | DATE RECEIVED | REPORT DATE AND TIME | REQUISITION NUMBER | COMMENT |
|---|---|---|---|---|
| | | | | |

LIPOPROTEIN PARTICLE RISK

| | | OPTIMAL | NEAR OPTIMAL | BORDERLINE-HIGH | HIGH | VERY HIGH |
|---|---|---|---|---|---|---|
| RISK$_{LDL/HDL}$ | 51 | <35 | 35 - 70 | 70 - 100 | 100 - 150 | >150 |

LDL-BASED RISK

| | nmol/L | OPTIMAL | NEAR OPTIMAL | BORDERLINE-HIGH | HIGH | VERY HIGH |
|---|---|---|---|---|---|---|
| RISK$_{LDL}$ | 2400 | <1000 | 1000 - 1399 | 1400 - 1799 | 1800 - 2200 | >2200 |

| | nmol/L | LOW | MODERATE | BORDERLINE | HIGH |
|---|---|---|---|---|---|
| LARGE LDL-P | 1200 | <300 | 300-499 | 500-800 | >800 |

| | nmol/L | LOW | MODERATE | BORDERLINE | HIGH |
|---|---|---|---|---|---|
| SMALL LDL-P | 600 | <500 | 500-849 | 850 - 1200 | >1200 |

HDL-BASED RISK

| | umol/L | OPTIMAL | NEAR OPTIMAL | BORDERLINE-LOW | LOW | VERY LOW |
|---|---|---|---|---|---|---|
| RISK$_{HDL}$ | 47 | >55 | 35 - 55 | 20 - 35 | 15 - 20 | <15 |

| | umol/L | LOW | MODERATE | BORDERLINE | HIGH |
|---|---|---|---|---|---|
| LARGE HDL-P | 11 | <2 | 2 - 5 | 6 - 12 | >12 |

| | umol/L | LOW | MODERATE | BORDERLINE | HIGH |
|---|---|---|---|---|---|
| MEDIUM HDL-P | 3 | <1 | 1 - 3 | 4 - 6 | >6 |

| | umol/L | LOW | MODERATE | BORDERLINE | HIGH |
|---|---|---|---|---|---|
| SMALL HDL-P | 19 | <12 | 12 - 17 | 18 - 23 | >23 |

FIGURE 3

METHODS, SYSTEMS AND COMPUTER PROGRAMS FOR ASSESSING CHD RISK USING ADJUSTED HDL PARTICLE NUMBER MEASUREMENTS

RELATED APPLICATIONS

This application claims the benefit of priority of U.S. Provisional Patent Application Ser. No. 60/746,894 filed May 10, 2006, the contents of which are hereby incorporated by reference as if recited in full herein.

FIELD OF THE INVENTION

The present invention relates generally to analysis of lipoproteins. The invention may be particularly suitable for NMR analysis of lipoprotein constituents in blood plasma and serum.

BACKGROUND OF THE INVENTION

In the past, "advanced" lipoprotein test panels have typically included a lipoprotein measurement of average low-density lipoprotein (LDL) particle size as well as LDL particle number, the latter representing the concentration or quantity (in concentration units such as nmol/L) and the former representing the average size of the LDL particles (in nm units) making up the LDL in the sample. For example, in the NMR LipoProfile® lipoprotein panel report available from LipoScience, Inc., located in Raleigh, N.C., the average LDL particle size corresponds to the average size of a sample's total LDL particles, i.e., the average size of the combined small, intermediate and large LDL particles. Any one person can have LDL particles present in a continuum of different particle sizes. See www.liposcience.com and U.S. Pat. No. 6,576,471 for exemplary reports of particular lipoprotein subclass parameters, the contents of the patent are hereby incorporated by reference as if recited in full herein.

Generally stated, U.S. Pat. No. 4,933,844, entitled Measurement of Blood Lipoprotein Constituents by Analysis of Data Acquired from an NMR Spectrometer to Otvos and U.S. Pat. No. 5,343,389, entitled Method and Apparatus for Measuring Classes and Subclasses of Lipoproteins, also to Otvos, describe NMR evaluation techniques that concurrently obtain and measure a plurality of different lipoprotein constituents in an in vitro blood plasma or serum sample. See also, U.S. Pat. No. 6,617,167, entitled Method Of Determining Presence And Concentration Of Lipoprotein X In Blood Plasma And Serum. The contents of all the above patents are hereby incorporated by reference as if recited in full herein. To evaluate the lipoproteins in a blood plasma and/or serum sample, the amplitudes of a plurality of NMR spectroscopy derived signals within a chemical shift region of the NMR spectrum are derived by deconvolution of the composite signal or spectrum and are compared to predetermined test criteria to evaluate a patient's risk of having or developing coronary artery or heart disease.

Conventionally, a patient's overall risk of coronary heart disease (CHD) and/or coronary artery disease (CAD), has been assessed based on measurements of cholesterol content of a patient's LDL and HDL particles (LDL-C, HDL-C) rather than the numbers of these particles. These two risk factors are used to assess a patient's risk, and treatment decisions may be made to reduce the "bad" cholesterol (LDL-C) or increase the "good" cholesterol (HDL-C). A convenient combined risk factor is the ratio of LDL-C/HDL-C (or more commonly used is the ratio of Total Cholesterol/HDL-C, which is almost the same thing)—to give an overall assessment of risk based on the relative amounts of LDL and HDL. Many physicians like the simplicity offered by the ratio and it is often used to gauge the success of LDL and/or HDL treatment interventions. If only the ratio is reported, however, the doctor won't know whether to direct therapy to reduce the numerator (LDL) or increase the denominator (HDL). So LDL-C and HDL-C plus the ratio are generally reported. Unfortunately, HDL-C does not adequately reflect the numbers of HDL subclass particles and may not be representative of a person's true HDL-related risk of having or developing CHD. In view of the foregoing, there remains a need to provide improved predictive models for assessing a person's risk of developing or having CHD.

SUMMARY

Certain embodiments of the present invention are directed at providing methods, systems, and computer program products with at least one adjusted measure of HDL particles of a discrete size range taken from a blood plasma or serum sample that may provide a better and/or easier to understand risk number to facilitate patient risk stratification and enable more effective treatment decisions compared with use of conventional markers of LDL-based risk alone, with HDL cholesterol (HDL-C) or with the ratio of LDL-C/HDL-C.

The adjusted measures may employ a mathematical model that can provide a "Good Particle Index". Adjusted measures of LDL subclass particles may also be generated to provide a "Bad Particle Index". A ratio of the Bad/Good particle indexes may also be generated as a Lipoprotein Particle Index and reported as an alternative to TC/HDL-C or LDL-C/HDL-C ratios to improve and/or increase the predictive power of a CHD risk analysis over a population. The predictive risk assessment number and/or models may be particularly useful for both automated screening for CHD risk and making more effective therapeutic management decisions to lower the risk of the patient for CHD.

Embodiments of the invention are directed to methods of determining a subject's risk of having and/or developing CHD. The methods include: (a) obtaining concentration measurements of small and large HDL subclass particles in a blood plasma or serum sample; (b) programmatically adjusting at least one of the small and large HDL subclass particle measurement values; and (c) determining a subject's risk of having and/or developing CHD based on the at least one adjusted HDL subclass particle measurement number.

Some embodiments of the invention are directed to methods for determining a subject's risk of CHD that include: (a) obtaining NMR derived concentration measurements of small and large HDL subclass particles in a biosample of interest; (b) applying a weighting factor to at least one of the measured large and small HDL particle concentrations; and (c) calculating an HDL risk predictor number using the weighted HDL particle concentration(s).

Other embodiments are directed to computer program products for adjusting measured in vitro concentrations of HDL particles to assess CHD risk. The computer program product includes a computer readable storage medium having computer readable program code embodied in the medium. The computer-readable program code includes computer readable program code that adjusts measured in vitro concentrations of at least one of small and large HDL particle subclasses to generate an HDL risk number to reflect a subject's risk of having or developing CHD.

Still other embodiments are directed to a system for obtaining data regarding lipoprotein constituents in a subject. The system includes: (a) an NMR spectrometer for acquiring at least one NMR spectrum of an in vitro blood plasma or serum sample; and (b) a controller in communication with the NMR spectrometer, the controller comprising a computer readable storage medium having computer readable program code embodied in the medium. The computer-readable program code includes: (i) computer program code for determining concentrations of small and large HDL particle subclasses in the sample undergoing analysis; and (ii) computer program code for adjusting at least one of the determined small and large HDL particle concentrations to determine a risk of developing or having CHD.

The method may optionally include calculating a LDL lipoprotein risk parameter number using at least two of small, medium and large LDL particle concentration values where the concentration values are increased relative to the measured small LDL particle concentration.

In particular embodiments, the method may include calculating a lipoprotein particle index from a ratio of the LDL risk parameter value to the HDL risk parameter value and may also include generating a patient-specific report presenting the LDL risk parameter value and the HDL risk parameter value along with a patient's risk of CHD based on the presented values.

Other embodiments are directed to methods of assessing CHD risk in a patient. The methods include: generating a single risk predictor variable using a ratio of a weighted LDL particle number as a numerator and a weighted HDL particle number as a denominator. The method can be implemented as a computer program product.

As will be appreciated by those of skill in the art in light of the present disclosure, embodiments of the present invention may include methods, systems, apparatus and/or computer program products or combinations thereof.

BRIEF DESCRIPTION OF THE FIGURES

FIG. 3 is an exemplary report that uses a HDL Risk number and may optionally use a HDL Risk number to reflect a subject's HDL-based risk according to embodiments of the present invention.

Figure 1:
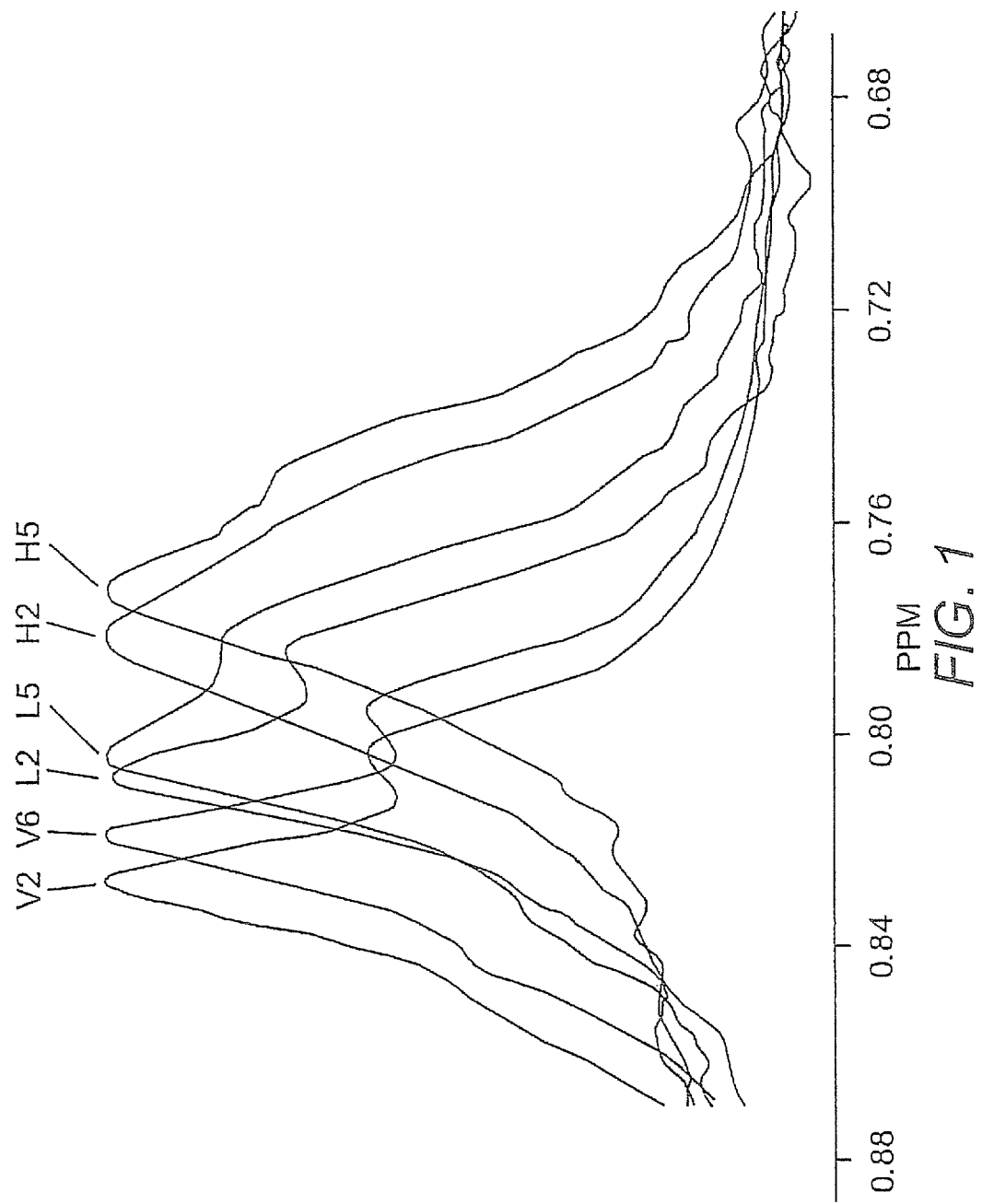
FIG. 1 is a graph showing the chemical shift spectra of a representative sample of lipoprotein constituent subclasses.

The foregoing and other objects and aspects of the present invention are explained in detail in the specification set forth below.

DETAILED DESCRIPTION OF EMBODIMENTS OF THE INVENTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "programmatically" means carried out using computer program directed operations. The terms "automated" and "automatic" means that the operations can be carried out with minimal or no manual labor or input. The term "semi-automated" refers to allowing operators some input or activation, but the calculations and signal acquisition as well as the calculation of the concentrations of the ionized constituent(s) is done electronically, typically programmatically, without requiring manual input.

Embodiments of the invention recognize that CHD risk is contributed to independently by high numbers of "bad" LDL particles and low numbers of "good" HDL particles. LDL particles can create atherosclerosis by entering the artery wall, becoming oxidized, and then being ingested by macrophages to create cholesterol-rich foam cells, which grow into the atherosclerotic plaque. HDL particles can enter the artery wall and prevent or reverse this process by 1) inhibiting the oxidation of LDL particles and 2) removing cholesterol from the foam cells and delivering it back to the liver—a process called reverse cholesterol transport. The overall risk of CHD depends on the balance between the bad and good particles.

As is generally accepted, HDL-cholesterol and/or LDL-cholesterol levels provided by conventional lipid panels fail to sufficiently differentiate populations with and without CHD or CAD. As is known to those of skill in the art, the Framingham study proposed a relatively lengthy risk model that considers many factors such as age, gender, smoking habits, as well as cholesterol values. The research conducted in the Framingham Offspring Study also defined normative and at-risk population values from subjects in the study. See Wilson et al., *Impact of National Guidelines for Cholesterol Risk Factor Screening The Framingham Offspring Study*, JAMA, 1989; 262: 41-44.

Unfortunately, many patients and clinicians still refer to total cholesterol and/or LDL-C and HDL-C to define a risk of developing CAD and/or to determine whether to begin or alter a therapeutic treatment. Thus, a simple, recognizable, easy- to-use more reliable risk factor may facilitate treatment for at-risk patients currently going undetected.

The present invention recognizes that lipoprotein particle physiology and/or properties can provide a better indicator of atherogenicity implicit to the lipoproteins that carry cholesterol. Because it is the number and size of lipoproteins that determine one's risk of heart disease (not one's cholesterol levels), drug therapy is typically targeted to reduce the number of LDL particles and/or increase the number of HDL particles. Embodiments of the present invention are directed to providing easy to recognize risk numbers that may facilitate treatment and follow-up that a patient and a clinician can use to more reliably assess risk relative to the cholesterol risk factors commonly used. More aggressive treatments may be desired when certain LDL particle subclasses are present in borderline and/or increased amounts and/or when certain HDL particle subclasses are present in borderline and/or decreased amounts relative to the general population or a clinical baseline.

It is contemplated that, just as LDL-C does not adequately reflect the numbers of different LDL subclass particles and take into account their differential atherogenicities, HDL-C does not adequately reflect the numbers of HDL subclass particles, not all of which are equally anti-atherogenic (i.e., conferring different degrees of protection from atherosclerosis). While not wishing to be bound to any one theory, it is contemplated that some HDL subclass particles may be better antioxidants or more effective mediators of reverse cholesterol transport. Thus, embodiments of the present invention weight the HDL subclasses and combine the values in a HDL risk parameter that may provide better risk prediction than that given by total HDL-P or HDL-C. Also, embodiments of the present invention weight the LDL subclasses and combine the values in a LDL risk parameter that may provide better risk prediction than that given by total LDL-P or LDL-C.

It is currently believed that exemplary numbers that patients would have for these weighted risk parameters may be:

(a) the weighted $R_{HDL}$ numbers would range from about 10-80 μmol/L:

(b) the $R_{LDL}$ range would be about 500-3,000 nmol/L; and (c) the ratio lipoprotein particle risk parameter ($R_{LDL}/R_{IDL}$) may vary from about 6 to 300.

Different therapies that increase HDL-C by the same amount may not increase the HDL subclasses proportionately. Some drugs, for example, increase HDL-C mainly by increasing the number of small HDL particles (such as those in the fibrate class). Others increase mainly large HDL-P. The weighted HDL index will change differentially with different therapies, indicating greater or lesser clinical benefit and may provide increased clinical data for evaluating therapeutic efficacy.

Presently, the LDL particle sizes are characterized as Pattern A (large) and Pattern B (small). Pattern A can be defined as large average particle sizes which typically includes sizes of between about 20.5-23.0 nm. Pattern B can be defined as smaller average particle sizes between about 18.0-20.5 nm.

As used herein, the term "small LDL particles" can include particles whose sizes range from between about 18.0 to about 21.2 nm. Alternatively, they can include particles in the very small (between about 18.0-19.8 nm) and intermediate small (between about 19.8-21.2 nm) diameter ranges. The term "large LDL particles" can include particles ranging in diameter between about 21.2-23.0 nm. Intermediate sized small particles may be parsed into one of the small and/or large designations or be measured separately as including particles in a size range that is typically near about 20.5 nm. It is noted that the LDL subclasses of particles can be divided in other size ranges. For example, small may be between about 18.0-20.5 nm, intermediate may be between about 20.5-21.2 nm, and large may be between about 21.2-23 nm. In addition, intermediate-density lipoprotein particles ("IDL" or "IDL-P"), which range in diameter from approximately 23.0-27.0 nm, can be included among the particles defined as LDL.

As used herein, the term "HDL subclasses" refers to size groupings of HDL particles. The predictive mathematical (HDL subclass risk) model can be used with NMR signal measurement methods that measure lipoprotein constituents using signals having spectral contribution from chemical constituents having overlapping signals. In certain embodiments, the HDL subclass size ranges may be further defined as three, or even more, different discrete and measurable constituents (i.e., H1, H2, H3, H4) and each may be individually weighted according to the mathematical model.

The term "large HDL particles" ("large HDL-P") can include HDL subclasses of particles whose sizes range from between about 8.8 to about 13 nm. The term "small HDL particles" (small HDL-P) can include particles ranging in diameter between about 7.3 to about 8.2 nm. The intermediate or medium HDL particles (medium HDL-P) can be parsed into one of the small or large designations or be measured separately as including particles in the size range that is typically between about 8.2 to 8.8 nm.

The terms CAD and CHD are used interchangeably to correspond to a patient or subject's risk of developing or having coronary artery and/or coronary heart disease, respectively.

The terms "population norm" and "standard" value associated with a lipoprotein measurement can be the values defined by the Framingham Offspring Study discussed below. However, the instant invention is not limited to these population values as the presently defined normal and at-risk population values for LDL particle concentrations or levels may change over time.

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

LDL is known to carry the so-called "bad" cholesterol. LDL particles come in different sizes. Conventionally, the smaller sizes have been thought to be the most dangerous type in that they were generally thought to be inherently more atherogenic than large particles. See, Sacks et al., *Clinical review 163. Cardiovascular endocrinology: Low density lipoprotein size and cardiovascular disease: a reappraisal*, J. Clin. Endocrinol Metab., 2003; 88: 4525-4532. Typical past studies examined only the distribution of LDL subclasses or LDL size phenotype (large or small) rather than particle concentrations of LDL subclasses. However, some studies have suggested that large LDL size may be associated with CHD. See, Campos et al., *Predominance of large LDL and reduced HDL2 cholesterol in normolipidemic men with coronary heart disease*, Arterioscler Thromb Vasc Biol., 1995; 15: 1043-1048; and Campos et al., *Low-density lipoprotein size, pravastatin treatment, and coronary events*, JAMA, 2001; 286, 1468-1474. Indeed, it is known that large LDL predominates in patients with familial hypercholesterolemia and those consuming high saturated fat diets. See, Patsch et al., *Characterization of lipoprotein in a kindred with familial hypercholesterolemia*, J. Lipid Res. 1982; 23:1196-1205; and Dreon et al., *Change in dietary saturated fat intake is correlated with change in mass of large low-density-lipoprotein particles in men*, Am. J. Clin Nutr 1998; 67: 828-836.

Despite the above, it is believed that, in the past, risk associated with small and large LDL particles was not compared on a per particle basis with control for the inverse correlation between small and large LDL particles. Also, the risk associated with small and large LDL particles was confounded due to their differing association with other lipoproteins and traditional cardiovascular risk factors. See e.g., Mora et al., *Both Large and Small LDL Particle Concentrations are Independently Associated with Carotid Atherosclerosis in the Multi-Ethnic Study of Atherosclerosis (MESA)*, Abstract presented at 2005 Scientific Sessions of the American Heart Association, Dallas, Tex., Circulation. 2005; 112: II-802. See also, Rosenson et al., *Relations of lipoprotein subclass levels and low density lipoprotein size to progression of coronary artery disease in the Pravastatin Limitation of Atherosclerosis in the Coronary Arteries (PLA C-1) trial*, Am J. Cardiol., 2002; 90:89-94. Embodiments of the instant invention weight LDL particles to assess risk recognizing that both large and small LDL subclasses are associated with atherosclerosis with insignificant (or no) additional contribution of LDL-C once the inverse correlation between the two subclasses is taken into account.

Not wanting to be limited to any one theory, it is contemplated that, on a per particle basis, large LDL particles (large LDL-p) can be associated with a greater amount of carotid atherosclerosis than small LDL particles (small LDL-p) and that small and large LDL are significantly associated with atherosclerosis independent of other risk factors. Carotid atherosclerosis measured non-invasively by ultrasound is closely related to all major cardiovascular risk factors and generally accepted to be a strong predictor of clinical cardiovascular disease. See, e.g., O'Leary et al., *Intima-media thickness; a tool for atherosclerosis imaging and event prediction*, Am. J. Cardiol., 2002; 90: 18L-21L.

The amount of cholesterol per LDL and HDL particle varies widely from person to person. One reason is that large LDL particles have higher cholesterol content than small LDL particles. But even among people with exactly the same numbers of small and large LDL particles, LDL cholesterol levels vary because of differences in the relative amounts of cholesterol and triglycerides inside the particles. As a consequence, LDL cholesterol levels are an imperfect surrogate measure of a patient's LDL particle numbers and the CHD risk that these particles confer. See, e.g., Cromwell et al., *Low-density lipoprotein particle number and risk for cardiovascular disease*, Curr. Atheroscler. Rep., 2004; 6:381-387.

The present invention recognizes that large and small LDL particles do not confer exactly the same CHD risk and large and small HDL particles do not confer the same CHD protection. As a result, an improvement in risk prediction may be realized by employing at least one weighting factor that adjusts the measurement of one or more different HDL particle subclasses. In some embodiments, the risk assessment may also optionally employ at least one weighting factor to adjust the measurement of one or more different LDL particle subclasses to account for their different contributions to atherosclerosis.

Figure 2:
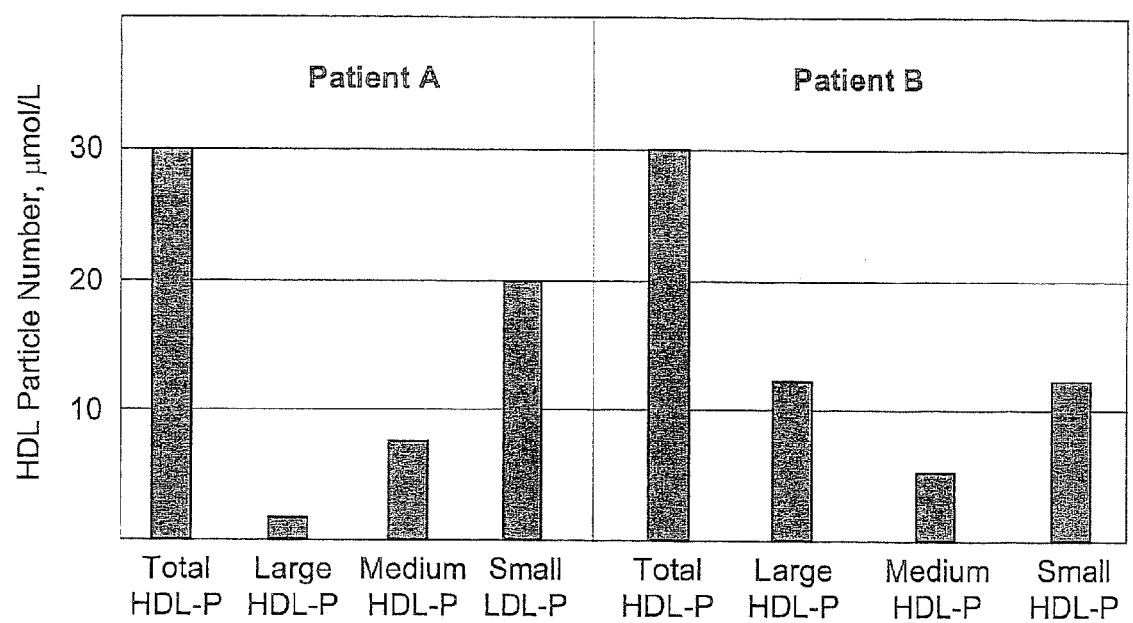
FIG. 2 is a schematic illustration of the dissimilar HDL subclass particle compositions of two patients, both of whom have the same total number of HDL particles but dissimilar HDL-based risk of CHD as recognized according to embodiments of the present invention.

As an example, as shown in FIG. 2, consider two patients with the same number of total HDL particles (HDL-P). Patient A has a smaller number of large HDL particles and more small HDL particles than Patient B. If large HDL particles, on a per particle basis, provide greater anti-atherogenic protection (associated with a lesser CHD risk), then the risk of Patient A would be greater than that of Patient B.

Similarly, consider two patients with the same number of LDL particles (LDL-P). Patient A has a greater number of large LDL particles and fewer small LDL particles than Patient B. If large LDL particles, on a per particle basis, confer greater CHD risk, then the risk of Patient A would be greater than that of Patient B.

Table 1 compares prophetic carotid atherosclerosis data (as measured by carotid ultrasound and expressed as the increase in intima media thickness "IMT", associated with a given increment in concentration of large or small LDL) to illustrate that it can take more (shown as more than twice as many) small LDL particles to cause the same increase in atherosclerosis as are caused by a lesser number of large LDL particles. As shown in this particular example, large LDL particles can be more (such as about 1.5-2.5 times more) atherogenic per particle than small LDL particles.

This data is believed to be generally representative of findings in a study carried out using data from patients enrolled in the Multi-Ethnic Study of Atherosclerosis (MESA). See the Examples Section hereinbelow.

TABLE 1

LDL Particle Risk

| Type | Increment | Increase in IMT |
|---|---|---|
| Large LDL particles (nmol/L) | 220 | 40 microns |
| Small LDL particles (nmol/L) | 450 | 40 microns |

While not wishing to be bound by any one theory, it is possible that in vivo a relatively steady-state concentration of small LDL particles may travel from the blood stream past the endothelial cells and into the arterial intima due to their smaller size and/or cellular make-up, but that large LDL particles carry more atherogenic material, so a deposit of lesser numbers of large LDL particles can be problematic as well. Thus, a weighting factor applied to measures of large and/or small LDL particles in blood plasma and/or serum samples can provide a risk indicator of CAD risk.

In the past, an average LDL particle size of 20.5 nm might result from a sample having no large and no small LDL particles (all intermediate) as well as a sample having 50% large and 50% small (averaging to an intermediate particle size). Hence, for a similar total LDL particle number, the CHD-risk for each of these samples may be different, but previously perhaps not clearly stated or easily recognized.

Certain embodiments of the present invention are directed at providing methods, systems, and computer program products that use HDL risk numbers (or mathematical models) that employ adjusted values of discrete measures of concentration of HDL (HDL subclasses of different (predetermined) particle size ranges) that may simplify, improve and/or increase the predictive power of a risk analysis over a population. The models may be particularly useful in automated screening tests and/or risk assessment evaluations for CAD screening of in vitro biosamples.

In certain embodiments, a predetermined mathematical HDL subclass risk model can be configured to evaluate each measured amount of target (predetermined) HDL subclass, then determine the value of a predictor variable based on adjusted measurements of at least one different subclass (size range) of HDL particles. Embodiments of the invention can analyze samples to provide discrete concentration measurements for both small HDL particles and large HLDL particles, recognizing that each size category has some degree of anti-atherogenicity, and then calculate a predictor value ($Risk_{HDL}$) considering each HDL subclass measurement.

Certain embodiments of the present invention can also use LDL risk numbers (or mathematical models) that employ adjusted values of discrete measures of concentration of LDL (LDL subclasses of different (predetermined) particle size ranges) that may simplify, improve and/or increase the predictive power of a risk analysis over a population.

In particular embodiments, an HDL particle risk predictor index or number ($Risk_{HDL}$) and an LDL particle risk predictor index or number ($Risk_{LDL}$) can be calculated by multiplying a weighting factor to at least one HDL subclass and at least one LDL subclass measurement. FIG. 3 illustrates an exemplary patient test report of $R_{HDL}$ and $R_{LDL}$ as well as an overall risk index of the ratio of the risk parameters, $R_{LDL}/R_{HDL}$ each of which can be used as a CHD risk assessment guide.

For the HDL risk index, the weighting can be applied to either or both the amount of small HDL particles ($HDL_S$) and/or to the large HDL particles ($HDL_L$) measured in the sample. If the weighting factor is only applied to the $HDL_S$ concentration, then it is presently contemplated that the weighting factor should be less than one, such as between about 0.25-0.75, and may be between about 0.5-0.7. If the weighting factor is applied only to the $HDL_L$ measurement, then the weighting factor may be between about 1.1 to about 3, and may be about 2.2+/−0.3. Exemplarily weights based on per particle measurements are provided below in Table 4. Optimal weighting factors may be confirmed with data from further studies.

Similarly, for the LDL risk index, the weighting can be applied to either or both the amount of small LDL particles ($LDL_S$) and/or to the large LDL particles ($LDL_L$) measured in the sample. If the weighting factor is only applied to the $LDL_S$ concentration, then it is presently contemplated that the weighting factor should be less than one, such as between about 0.25-0.75, and may be between about 0.5-0.7. If the weighting factor is applied only to the $LDL_L$ measurement, then the weighting factor may be between about 1.1 to about 2, and may be about 1.5+/−0.3. Exemplarily weights based on per particle measurements are provided below in Tables 2 and 3. Optimal weighting factors may be confirmed with data from further studies.

This LDL risk model may be expressed using the following mathematical equation:

$$X(LDL_S)+Y(LDL_L)=Risk_{LDL} \text{(e.g., the bad particle index)}$$

The HDL risk model may be expressed using the following mathematical equation:

$$X'(HDL_S)+Y'(HDL_L)=Risk_{HDL} \text{(e.g., the good particle index)}$$

where X, X' or Y, Y' can be one, typically X, X'=1 and Y,Y'>1, and/or where Y, Y'>X, X'. In some embodiments, both weighting factors X, X' and Y, Y' may be above 1.

In other embodiments, a third weighting factor "Z" can be used to add intermediate LDL particles and/or IDL particles to the LDL risk model and medium HDL particles ($HDL_M$) to the HDL risk model.

$$Z(IDL-P)+X(LDL_S)+Y(LDL_L)=Risk_{LDL}$$

$$Z'(HDL_M)+X'(HDL_S)+Y'(HDL_L)=Risk_{HDL}$$

For LDL, the third weighting factor Z may be greater than that of X and Y, and may have a value that is increased between about 4-6 above LDLs (relative to measurement of the small LDL particles). Hence, in certain embodiments: Z>Y>X. For HDL, the third weighting factor Z' may be less than Y' and greater than X', such as a value that is about 30-50% greater than X' but about 30-50% less than Y'. The X', Y' and/or Z' values used for $R_{HDL}$ are typically different from X, Y, Z used for $R_{LDL}$. Additional weights and particle subclass subdivisions may be used. As an alternative to linear models primarily discussed herein, a multi-factorial (non-linear) model can be used to automatically calculate a risk number using an adjusted LDL or HDL subclass measurement obtained electronically based on a measurement of a biosample without requiring clinician input on non-automatically measured parameters (such as BMI, smoking habits and the like). The HDL or LDL subclass measurements can be combined and adjusted to automatically generate the HDL or LDL particle risk number and/or weighted risk index, which can be electronically tracked over time.

In certain embodiments, X can be weighted above 1 and Y can be weighted above 1, to reflect the measured concentrations of the LDL particles' contribution to risk. In some embodiments, X can be weighted with a weighting factor that is below 1 and Y can be at about 1 or greater than 1. In other embodiments, X and Y can have weighting factors that are below 1, with Y being greater than X for certain or all measures of large LDL particle concentrations. In some embodiments, the subclass measurements can be adjusted so that the large LDL subclass measurement reflects between a 1.5-3 fold multiplier over the small LDL subclass measurement.

In particular embodiments, Y can be selected to increase the measured value of large LDL particles by at least about 25% relative to the small LDL particle measurement.

The weighting factors X, X', Y, Y' (and/or Z, Z') in the LDL and/or HDL risk model, respectively, may be constants applied across substantially all samples. In other embodiments, the weighted values may be defined in situ and/or applied using a formula or a programmatically implemented or directed look-up table, based on a particular sample's contents. For example, X and Y and/or X', Y' may vary depending on age, gender, or other patient factor and/or based on the total number or HDL or LDL particles present, and/or the amount of each subclass particle measured relative to the general population, and/or as a percentage of the particles. For example, where large LDL subclass particles are present in an amount greater than the median value of the general population, a higher than normal weight can be assigned to Y. Where both small LDL particles and large LDL particles are present in amounts greater than the median of the general population, and/or the total LDL particle number is borderline or high, Y and/or both X and Y may be assigned a greater value compared to those situations where large and/or small LDL subclass particle numbers are less than the population median.

In certain embodiments, the model is configured to apply at least one different increased weighting factor, as increased concentrations of the small and/or large HDL or LDL particles are determined. Thus, for high levels of particular HDL or low levels of LDL particle subclass concentrations, the risk model used to determine the risk number may not apply any weighting factors to the measured values of small and/or large subclass particle concentrations to arrive at the risk number. However, as the total or individual concentrations of respective subclass particles exceed a predetermined threshold level, a weighting factor(s) or altered weighting factor can then be applied.

The predictive model can be used with any suitable HDL or LDL subclass measurement technique, including, but not limited to, gradient gel electrophoresis, density gradient ultracentrifugation, and NMR spectroscopy. However, in particular embodiments, the predictive model may be used with NMR spectroscopy measurements of HDL and LDL subclasses in in vitro blood plasma and/or serum samples.

In operation, to obtain the value of the predictor risk variables $R_{HDL}$ and $R_{LDL}$, particle concentration measurements of at least large and small HDL and/or LDL particles in a sample of interest can be obtained (such as in nmol/L units or other suitable metric). If using NMR spectroscopy, then, similar to conventional techniques for NMR-derived particle concentration measurements, particle concentrations (nanomoles of particles per liter, nmol/L) for small and large HDL and/or LDL subclass particles can be calculated by measuring the signal amplitudes broadcast by these subclasses and applying conversion factors derived from the NMR measurements of isolated subclass standards of known particle concentration. The particle concentrations of the large and small HDL and/or LDL subclasses can then be adjusted (such as, for example, multiplied by their weighting factors (X, X', Y, Y' etc.) and added together to provide the value of the $R_{HDL}$ and/or $R_{LDL}$ (also typically in nmol/L)).

For example, compare two prophetic measurements of large and small LDL concentrations in two different patients, each having a total LDL particle number that is substantially the same, using the X (1.25) and Y (2.5) weighting factors to calculate an associated LDL risk number.

Patient (1)

$L\text{-}LDLp$ 600 nmol/L $S\text{-}LDLp$ 800 nmol/L $Risk_{LDL} = [(X)(800) + (Y)(600)] = 2500$ Patient (2)

$L\text{-}LDLp$ 400 nmol/L $S\text{-}LDLp$ 1000 nmol/L $Risk_{LDL} = [X(1000) + Y(400)] = 2250$ In other embodiments, the two prophetic measurements of large and small LDL concentrations in the two different patients can be adjusted using X=1 and Y=1.5 (making X=1 and adjusting Y so that the weighted large LDL measurement can generate the relative increase in risk) to calculate an associated LDL risk number.

Patient (1)

$Risk_{LDL} = [(X)(800) + (Y)(600)] = 1700$

Patient (2)

$Risk_{LDL} = [X(1000) + Y(400)] = 1600$

Thus, although each patient has a similar total LDLp number, patient (1) has a higher risk of CAD than patient (2) according to the LDL risk number. Similar weighted measurements can be used to determine $Risk_{HDL}$.

For user ease of recognition, the risk number can be converted to a straight or scalar risk number, i.e., 1-10, or used as the risk number itself. For example, patients (1) and (2) can be assigned the risk number calculated above, or the number may be scaled in a particular way. For example, patient (1) may have a risk index of 8, while patient (2) may have a risk index of 7.

In contrast to previous analysis methods, two people having the same HDL particle number and LDL particle number may now have a different adjusted (weighted) HDL or LDL risk number based on a weighted concentration of one or more of the constituents that make up the HDL particle number or the LDL particle number, that may more appropriately represent the "true" HDL and LDL-based risk in the person having, for example, increased amounts of smaller HDL particles, without disregarding benefit from larger HDL particles and increased amounts of larger LDL particles without disregarding risk from smaller LDL particles.

In any event, conventionally, the first step in treating increased numbers of lipoproteins is identification. Embodiments of the present invention provide screening tests and reports that analyze the unique properties of lipoproteins to give complete quantitative and qualitative lipoprotein information. The test report can be configured to contain significant and unique information about an individual's underlying risk for CHD including the HDL risk predictor variable, $R_{HDL}$, and the LDL risk predictor variable, $R_{LDL}$ (i.e., the adjusted HDL and LDL particle numbers) that can be used to assess the HDL-particle and LDL particle-related risk in the lipoprotein risk analysis section as shown in FIG. 3. As noted above, particular embodiments of the present invention are directed to NMR-derived measurements of lipoproteins similar to a NMR LipoProfile® NMR-derived cholesterol or lipoprotein panel, which includes a $R_{HDL}$ and $R_{LDL}$ number as well as a total single risk number Risk LDL/HDL and may optionally include values for other lipoproteins of interest that may also be considered when evaluating a patient, including concentrations of subclasses of HDL and subclasses of VLDL.

Exemplary NMR Sample Analysis

As is known, an NMR lipoprotein subclass analysis can be carried out to measure lipoprotein subclass levels and average VLDL, LDL, and HDL particle diameters by NMR spectroscopy. The NMR method uses the characteristic signals broadcast by lipoprotein subclasses of different size as the basis of their quantification. See Otvos J D, Jeyarajah E J, Bennett D W, Krauss R M. *Development of a proton nuclear magnetic resonance spectroscopic method for determining plasma lipoprotein concentrations and subspecies distributions from a single, rapid measurement*, Clin Chem 1992; 38:1632-1638; and Otvos J, *Measurement of lipoprotein subclass profiles by nuclear magnetic resonance spectroscopy*, Clin Lab 2002; 48: 171-180. Each subclass signal emanates from the aggregate number of terminal methyl groups on the lipids contained within the particle, with the cholesterol esters and triglycerides in the particle core each contributing three methyl groups and the phospholipids and unesterified cholesterol in the surface shell each contributing two methyl groups. The total number of methyl groups contained within a subclass particle is, to a close approximation, dependent only on the particle's diameter and is substantially unaffected by differences in lipid composition arising from such sources as variability in the relative amounts of cholesterol ester and triglyceride in the particle core, varying degrees of unsaturation of the lipid fatty acyl chains, or varying phospholipid composition. For this reason, the methyl NMR signal emitted by each subclass serves as a direct measure of the particle concentration of that subclass.

In the past, NMR spectra of each plasma specimen (0.25 ml) were acquired in replicate (typically about 5 separate spectra are acquired) using an automated 400 MHz lipoprotein analyzer and the lipid methyl signal envelope decomposed computationally to give the amplitudes of the contributing signals of 16 lipoprotein subclasses (chylomicrons, 6 VLDL, 1 IDL, 3 LDL, 5 HDL). Conversion factors relating these signal amplitudes to subclass concentrations expressed in particle concentration units or lipid mass concentration units (cholesterol or triglyceride) were then applied. The conversion factors were derived from NMR and chemical analyses performed on a set of purified subclass standards of defined size, which were isolated from a diverse group of normo- and dyslipidemic individuals using a combination of ultracentrifugation and agarose gel filtration chromatography. Particle concentrations (in mol/L (nmol of particles per liter)) were calculated for each subclass standard by measuring the total concentration of core lipid (cholesterol ester plus triglyceride) and dividing the volume occupied by these lipids by the core volume per particle calculated from knowledge of the particle's diameter. Rifai N, Warnick G R, Dominiczak M H, eds: *Handbook of LipoProtein Testing, 2nd Edition*, Washington, D.C., AACC Press; 2000, pp 609-623. Lipid mass concentrations of VLDL subclasses are given in mg/dL triglyceride units and those of the LDL and HDL subclasses in mg/dL cholesterol units. Summing the relevant subclass concentrations gives NMR-derived values for total VLDL triglycerides, LDL cholesterol, and HDL cholesterol.

Conventionally, the 16 measured subclasses have been grouped for analysis into the following 10 subclass categories (but different size ranges may also be used as noted above): large VLDL (60-200 nm), medium VLDL (35-60 nm), small VLDL (27-35 nm), IDL (23-27 nm), large LDL (21.3-23 nm), medium LDL (19.8-21.2 nm), small LDL (18.3-19.7 nm), large HDL (8.8-13 nm), medium HDL (8.2-8.8 nm), and small HDL (7.3-8.2 nm). IDL and LDL subclass diameters, which are uniformly ~5 nm smaller than those estimated by gradient gel electrophoresis, are consistent with both electron microscopy and LDL lipid compositional data. See Redgrave T G, Carlson L A, *Changes in plasma very low density and low density lipoprotein content, composition, and size after a fatty meal in normo- and hypertriglyceridemic man*. J Lipid Res. 1979; 20:217-29; and Rumsey S C, Galeano N F, Arad Y, Deckelbaum R J. *Cryopreservation with sucrose maintains normal physical and biological properties of human plasma low density lipoproteins*, J Lipid Res 1992; 33:1551-1561.

Weighted average VLDL, LDL, and HDL particle sizes (nm diameter) were computed as the sum of the diameter of each subclass multiplied by its relative mass percentage as estimated from the amplitude of its methyl NMR signal. LDL and HDL subclass distributions determined by gradient gel electrophoresis and NMR are highly correlated. Otvos J D, *Measurement of lipoprotein subclass profiles by nuclear magnetic resonance spectroscopy*, Clin Lab 2002; 48:171-180; and McNamara J R, Small D M, Li Z, Schaefer E J, *Differences in LDL subspecies involve alterations in lipid composition and conformational changes in apolipoprotein B*, J Lipid Res 1996; 37:1924-1935; and Grundy S M, Vega G L, Otvos J D, Rainwater D L, Cohen J C. *Hepatic lipase influences high density lipoprotein subclass distribution in normotriglyceridemic men: genetic and pharmacological evidence*, J Lipid Res 1999; 40:229-234.

Replicate analyses of plasma pools indicate that NMR subclass measurements are reproducible, with coefficients of variation <3% for NMR-derived values for total and VLDL triglycerides, LDL and HDL cholesterol, and LDL particle concentration, <4% for VLDL size, and <1% for LDL and HDL average size. Otvos J D, *Measurement of lipoprotein subclass profiles by nuclear magnetic resonance spectroscopy*, Clin Lab 2002; 48:171-180.

As noted above, the conventional analysis technique described has been modified to be able to reliably quantify large and small LDL particle concentrations as described in the aforementioned co-pending U.S. patent application Ser. No. 10/691,103. The evaluation can be further modified to implement a predictive model to provide a weighted LDL risk number according to embodiments of the present invention.

An alternative NMR measurement technique is described in *Diffusion ordered nuclear magnetic resonance spectroscopy: principles and applications*, Prog. In NMR Spec, 34 (1999) 203-256. See also, WO 2005/119285 A1, *Process of Determination of Lipoproteins in Body Fluid*, the contents of which are hereby incorporated by reference as if recited in full herein.

In addition, as noted above, other evaluation techniques (including non-NMR measurement techniques) may also be used according to alternative embodiments of the present invention.

Statistical Operations

In certain embodiments, the methods, systems, and/or computer products used to evaluate specimens employ statistical fitting models which evaluate signal data of an unknown sample according to a predetermined fitting model and standards to identify the presence of at least one selected chemical constituent and/or to measure the level or concentration thereof in the sample. More typically, the models, programs, and methods of the present invention are configured to evaluate signal data of a composite sample with highly or closely correlated individual constituent spectra (having at least a plurality with overlapping signal lines in the spectrum) to identify the presence of at least 10 different individual constituents and/or the level thereof. The term "highly" and "closely" are used interchangeably when used with "correlated" so that in the description that follows either "highly correlated" or "closely correlated" means that a plurality of constituents in a sample being analyzed generate respective spectra which can overlap in a composite signal that includes spectral contributions from those constituents.

As will be appreciated by one of skill in the art, the present invention may be embodied as an apparatus, a method, data or signal processing system, or computer program product. Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java®, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

Figure 4:
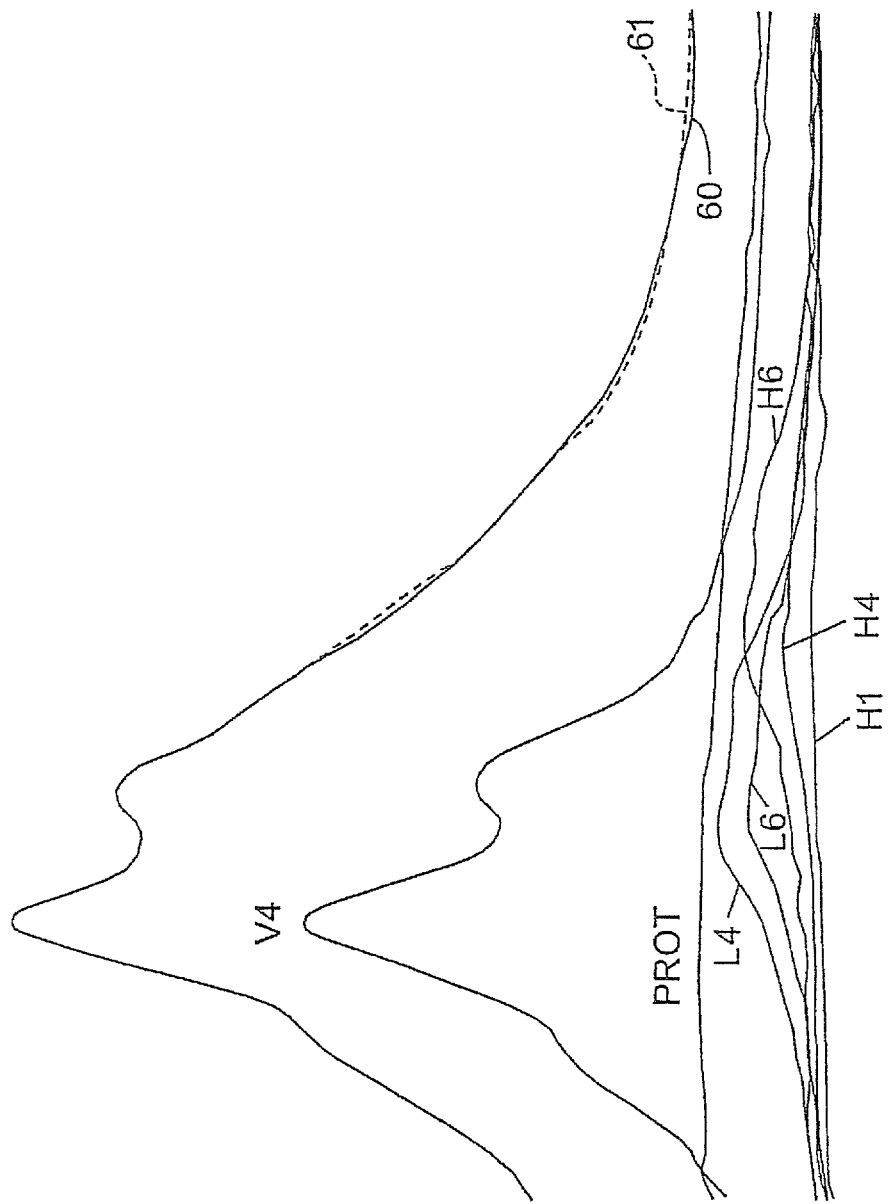
FIG. 4 is a graph illustrating NMR spectra for a composite plasma sample and the lipoprotein subclass and protein components thereof, with the peaks for methyl groups being illustrated.

The small person-to-person variations in the lineshapes of the lipoprotein classes are caused by the subclass heterogeneity known to exist within each of these lipoprotein classes. FIG. 1 shows the lineshapes and chemical shifts (positions) for a number of subclasses of lipoproteins. As shown in FIG. 1, the chemical shifts and lineshape differences between the different subclasses are much smaller than those between the major lipoprotein classes, but are completely reproducible. Thus, differences among the NMR signals from the plasma of individuals are caused by differences in the amplitudes of the lipid resonances from the subclasses present in the plasma, which in turn are proportional to their concentrations in the plasma. This is illustrated in FIG. 4, in which the NMR chemical shift spectra of a blood plasma sample is shown. The spectral peak produced by methyl ($CH_3$) protons 60 (shown as a solid line) is shown for the blood sample in FIG. 4. The spectral peak 61 (shown as a dotted line) in FIG. 4 is produced by the arithmetic sum of the NMR signals produced by the lipoprotein subclasses of the major classes VLDL, LDL, HDL, proteins and chylomicrons, as illustratively shown by certain of the subclasses in FIG. 1. It can be seen that the lineshape of the whole plasma spectrum is dependent on the relative amounts of the lipoprotein subclasses whose amplitudes change (sometimes dramatically) with their relative concentrations in the plasma sample.

Since the observed $CH_3$ lineshapes of whole plasma samples are closely simulated by the appropriately weighted sum of lipid signals of its constituent lipoprotein classes, it is possible to extract the concentrations of these constituents present in any sample. This is accomplished by calculating the weighting factors which give the best fit between observed blood plasma NMR spectra and the calculated blood plasma spectra. Generally speaking, the process of NMR lipoprotein analysis can be carried out by the following steps: (1) acquisition of an NMR "reference" spectrum for each of the "pure" individual or related groupings of constituent lipoprotein classes and/or subclasses of plasma of interest, (2) acquisition of a whole plasma NMR spectrum for a sample using measurement conditions substantially identical to those used to obtain the reference spectra, and (3) computer deconvolution of the plasma NMR spectrum in terms of the constituent classes and/or subclasses (or related groupings thereof) to give the concentration of each lipoprotein constituent expressed as a multiple of the concentration of the corresponding lipoprotein reference.

Although the procedure can be carried out on lipoprotein classes, carrying out the process for subclasses of lipoproteins can decrease the error between the calculated lineshape and the NMR lineshape, thus increasing the accuracy of the measurement while allowing for simultaneous determination of the subclass profile of each class. Because the differences in subclass lineshapes and chemical shifts are small, it is typically important to correctly align the reference spectrum of each subclass with the plasma spectrum. The alignment of these spectra is accomplished by the alignment of control peaks in the spectra, which are known to respond in the same manner to environmental variables, such as temperature and sample composition, as do the lipoprotein spectra. One such suitable alignment peak is the peak produced by CAEDTA, although other EDTA peaks or suitable peak may be utilized. By alignment of the spectra, the small variations in the subclasses' lineshapes and chemical shifts may be exploited to produce higher accuracy and subclass profiles.

Further description of these methods can be found in U.S. Pat. Nos. 4,933,844 and 5,343,389 to Otvos.

Lineshape

The mathematics used in the lineshape fitting process (i.e., least squares fit of an unknown function in terms of a weighted sum of known functions) is well known and is described in many textbooks of numerical analysis, such as F. B. Hildebrand, *Introduction to Numerical Analysis*, 2nd edition, pp. 314-326, 539-567, McGraw-Hill, 1975.

In particular embodiments, reference samples of each constituent lipoprotein and protein component to be analyzed are prepared (typically they are refrigerated during storage and allowed to warm prior to analysis) and placed within the spectrometer 10. An NMR measurement is then taken on each reference sample to define a standard for the respective constituent. The data for the reference samples (for a plurality of different constituents) is processed and stored in the computer 11. Techniques for acquiring and storing NMR spectroscopic data are well-known to those skilled in this art and need not be described in further detail. The reference samples or standards may be established a priori and used to measure a plurality of different patient specimens or samples over time.

To carry out the analysis, the data points of the real part of the sample plasma spectrum that comprise the spectral region to be fit (normally 0.73-0.85 ppm for lipoprotein evaluations) are entered into an array. This plasma array consists of m discrete data points denoted $P_i^o$, i=1,2, ... m. The data points of the real part of the lipoprotein subspecies *reference* spectra for the same spectral region are entered into separate arrays. The data points of these arrays are denoted $V_{ji}$, where i=1,2, ... m data points and j=1,2, ... n constituents). It is noted that in the Equations and text describing same that follows, some symbols may be bolded and/or italicized at certain locations but not at other locations, however this is not meant to alter the correlation or change the meaning of the symbol herein.

The method for fitting the measured sample plasma spectrum, $P_i^o$, with a linear combination of n constituent spectra is based on the premise that there are a set of coefficients (weighting factors), $c_j$, corresponding to the contributions of component j (lipoprotein subclass components and protein component), and a coefficient, $c_p^I$, corresponding to the imaginary portion of the sample plasma spectrum, such that for each data point, $P_i^o \cong P_i^c$, where $$P_i^c = \left(\sum_{j=1}^{n} c_j V_{ji}\right) + c_p^I V_i^I \quad (1)$$

(calculated plasma spectrum)

In the past, the best fit was achieved when the root mean square error, $$\sqrt{\frac{1}{m-n}(\sum \epsilon_i^2)} \quad (2)$$

was minimized, where $\epsilon_i = P_i^o - P_i^c$. This was accomplished by finding those coefficients which minimize $\Sigma \epsilon_i^2$, that is, when $$\frac{\partial \sum \epsilon_i^2}{\partial c_j} = 0, \quad (3)$$

j=1,2, ... n+1 (n−1 subspecies *components* plus protein and plasma spectrum phase contributions). Differentiation results in n+1 simultaneous linear equations:

$$\sum_{i=1}^{m} P_i^o V_{ki} = \sum_{j=1}^{n+1} c_j \left(\sum_{j=1}^{M} V_{ki} V_{ji}\right), k = 1, 2, \ldots n+1 \quad (4)$$

If $$a_{kj} = \sum_{j=1}^{m} V_{ki} V_{ji} \text{ and } s_k = \sum_{i=1}^{m} P_i^o V_{ki} \quad (5)$$

then there are n+1 simultaneous linear equations of the form:

$$\sum_{j=1}^{m} c_j a_{kj} = s_k, k = 1, 2, \ldots n+1 \quad (6)$$

Forming the n+1×n+1 matrix, [A]=[$a_{k_j}$], j=1,2 ... n+1; k=1, 2 ... n+1, gives [A]C=S, where C and S are the column vectors, $$\begin{bmatrix} c_1 \\ c_2 \\ \vdots \\ c_n \\ c_{n+1} \end{bmatrix} \text{ and } \begin{bmatrix} s_1 \\ s_2 \\ \vdots \\ s_n \\ s_{n+1} \end{bmatrix} \quad (7)$$

The coefficients providing the best fit were calculated by decomposition of the matrix [A] into a new set of m×m matrices known collectively as the "singular value decomposition" of [A]:

$$[A]=[U][W][V]^T \quad (8)$$

where [U] is a matrix of orthogonal column vectors (scalar products=0), $[V]^T$ is the transpose of an orthogonal matrix

[V], and [W] is a diagonal matrix with positive or zero elements, called "singular values:"

$$[W] = \begin{bmatrix} w_1 & 0 & \cdots & 0 \\ 0 & w_2 & \cdots & 0 \\ \vdots & \vdots & \ddots & \vdots \\ 0 & 0 & \cdots & w_m \end{bmatrix} \quad (9)$$

From this, $$[A]^{-1} = [V][W]^{-1}[U]^T \quad (10)$$

where $$[W]^{-1} = \begin{bmatrix} 1/w_1 & 0 & \cdots & 0 \\ 0 & 1/w_2 & \cdots & 0 \\ \vdots & \vdots & \ddots & \vdots \\ 0 & 0 & \cdots & 1/w_m \end{bmatrix} \quad (11)$$

which allows C to be solved for:

$$C = [V][W]^{-1}[U]^T S \quad (12)$$

where C was the best possible solution vector, provided that values of $w_j$ below a certain threshold value (selected by the user) are ignored ($1/w_j$ set to zero). These singular values can give rise to "ill-conditioned" linear combinations of near degenerate solutions, being most corrupted by roundoff errors. The actual solution of C was obtained by "back-substitution" in which $w_m$ is determined, allowing for the solution of $w_{m-1}$, etc.

The root mean square deviation (RMSD) is computed as $$\sigma\text{RMS} = \sqrt{\frac{1}{m-n-1} \sum_{i=1}^{m} (P_i^o - P_i^c)^2} \quad (13)$$

The correlation coefficient was computed as $$r^P = \frac{\sum_{i=1}^{m} (P_i^o - \langle P_i^o \rangle)(P_i^c - \langle P_i^c \rangle)}{\sqrt{\left(\sum_{i=1}^{m} (P_i^o - \langle P_i^o \rangle)^2 \sum_{i=1}^{m} (P_i^c - \langle P_i^c \rangle)^2\right)}} \quad (14)$$

In the past, the component coefficients resulting from this lineshape analysis provided the concentrations of the lipoprotein and protein constituents in each plasma sample. Each concentration can be expressed relative to the concentration of the lipoprotein whose spectrum is used as the reference. In operation, the final concentrations may be normalized to the integrated area of the resonance from a tri-methylacetate external standard sample run on the same day to correct for variations in the detection sensitivity of the NMR spectrometer.

As described above, the least squares method used in the past for NMR-derived measurement of lipoprotein subclasses required that the derived concentrations be a positive value. Generally described, in the past, when a negative coefficient for a selected constituent associated with one of the standards was encountered it was constrained to zero, and the calculation was performed again, subject to that constraint. The latter constraint can be desirable when fitting plasma samples that may not contain one or more of the components included in the fit model or because experimental errors in the data (noise) can cause the calculation to give negative values for concentrations for these components.

Figure 5:
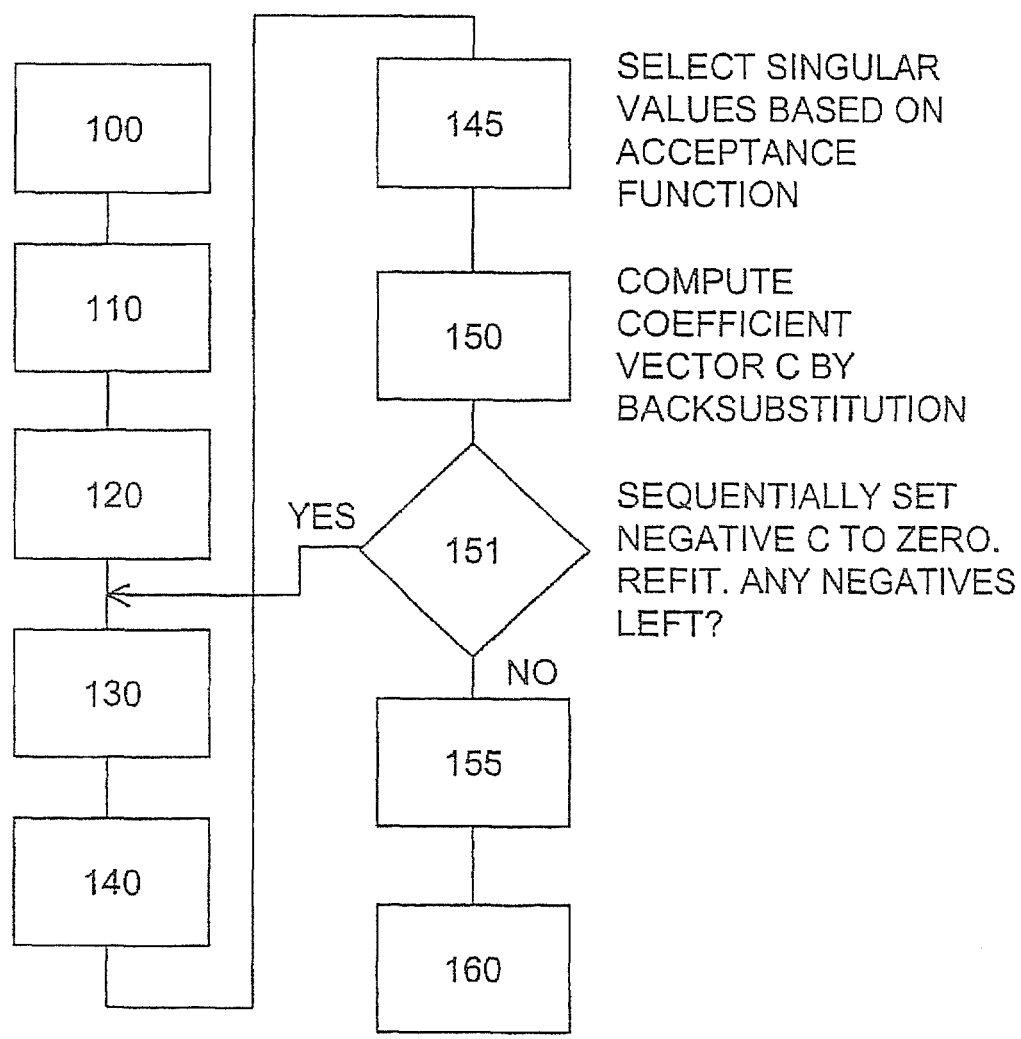
FIG. 5 is a block diagram of operations that can be used to evaluate signal data according to embodiments of the present invention.

FIG. 5 illustrates a flow chart of operations with reference to certain of the above-stated equations in blocks 100-160. In operation, spectra of subspecies *components* are read into Array V (block 100). The real part of the sample plasma spectrum is read into Array $P^O$ (block 110). The imaginary part of the sample plasma spectrum is read into the Array V (block 120). Marix [A] and S vector are calculated (block 130) using Equation 5. Matrix [A] is decomposed into a singular value decomposition (block 140) such as by using Equation 8. The singular values are selected based on a predetermined acceptance function (block 145). The coefficient vector C is calculated using back substitution (block 150). The negative values in C are sequentially set to zero and the curve is refit, until there are no negatives left. The yes or no inquiry at (block 151) asks whether there are negatives left and, if so, directs the program to return to the operation in (block 130) and, if not, directs the operations to advance to (block 155). C is multiplied by normalization constants to obtain concentrations (block 155). The root mean square deviation and correlation coefficient are calculated (block 160) such as by using Equations 13 and 14.

Embodiments of the present invention modify and improve on the conventional protocol by employing operations that can reduce measurement variability in individual constituents and/or by reducing the number of constituents of interest that are reported as having a "0" value. The variability can be assessed by repeatedly analyzing a given sample and measuring the individual constituents. The individual constituents measured by the present invention will typically be clustered more tightly together relative to the individual constituents measured by the conventional protocol. The methods and systems can reduce the variability by at least about 50% relative to the prior method for the same sample. Further, when analyzing the same sample in repeated interrogations, the measured values of at least a majority of the constituents of interest, if not all of the constituents of interest, can be reproducible, typically within about +/−2.34% (median CV).

Figure 6:
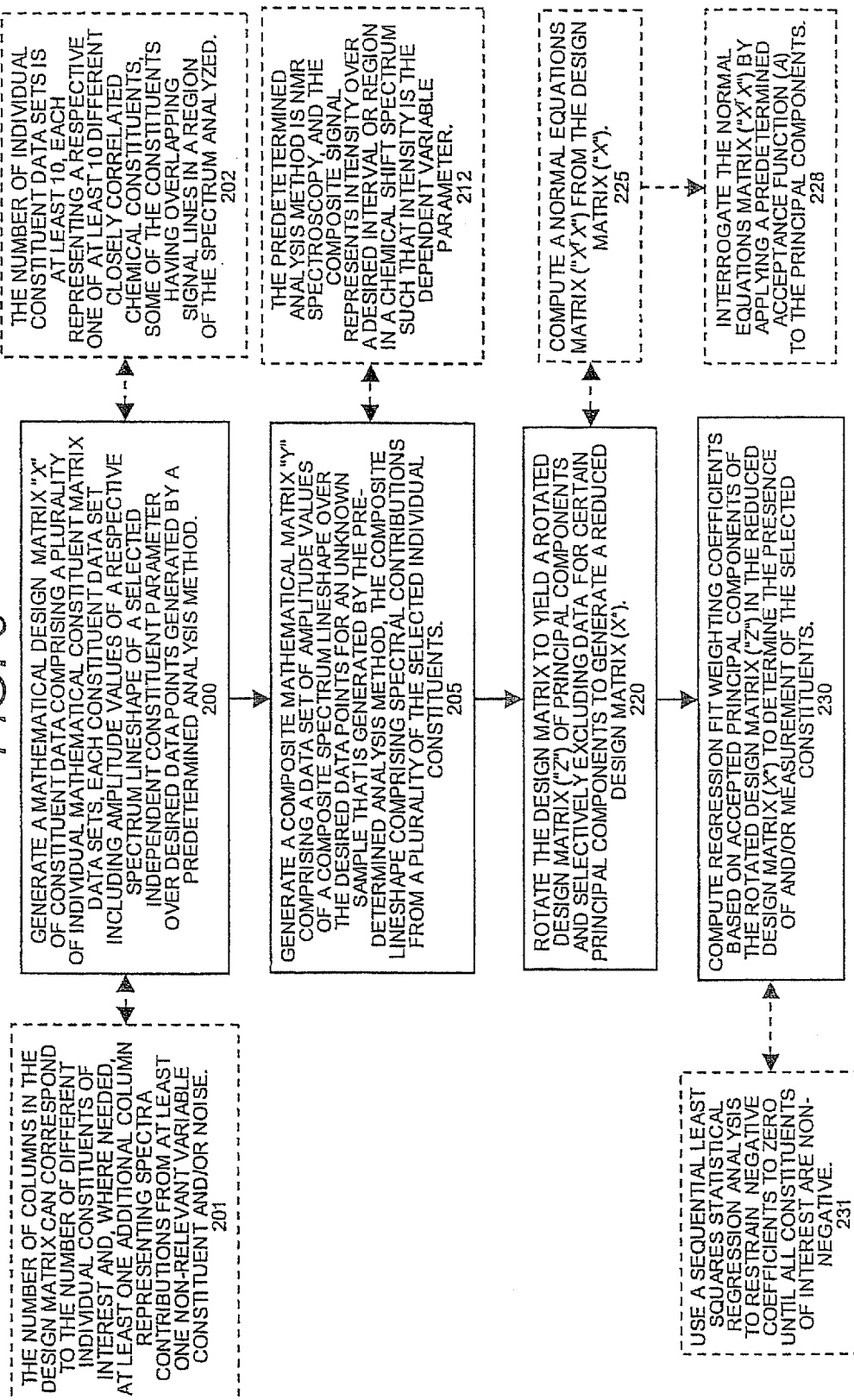
FIG. 6 is a block diagram of operations that can be used to evaluate signal data according to embodiments of the present invention.

Referring now to FIG. 6, operations of certain embodiments of the invention are illustrated. It is noted that the term "matrix," as used herein, can, in certain embodiments, be a vector, as a vector is a special form of a matrix (i.e., a vector is a matrix with n rows and 1 column, or 1 row and k columns). As shown in FIG. 6, the operations can include generating a mathematical design matrix of constituent data comprising a plurality of mathematical constituent matrix data sets, each constituent data set including amplitude values of a respective spectrum lineshape of a selected independent constituent parameter over desired data points generated by a predetermined analysis method (of a known reference sample) (block 200). The selected constituent parameter (the independent parameter) can be wavelength, voltage, current, speed, force, torque, pressure, movement, energy, chemical shift (ppm), temperature, and frequency. Exemplary dependent parameters of interest may include, but are not limited to, intensity, opacity, transmittance, reflectance, fluorescence, vibration, or other desired parameter. The constituent data of the design matrix ("A") can be reference or standard data established a priori from separate individual analysis of discrete constituents of interest and/or stored in an accessible database to be used as a standard and applied in analysis of all or selected ones of unknown samples.

A composite mathematical matrix can be generated comprising a data set of amplitude values of a composite spectrum lineshape over the desired data points for an unknown sample that is generated by a predetermined analysis method. The composite lineshape comprises spectral contributions from a plurality of the selected individual constituents (block 205). The design matrix can be rotated to yield a rotated design matrix of principal components (which may, in certain embodiments, be mathematically represented by matrix "Z" as will be discussed further below) and processed to selectively exclude data for certain principal components to generate a reduced design matrix (which may, in certain embodiments, be represented mathematically by matrix "X*" as will be discussed further below) (block 220). The term "principal components" means individual identifiable constituents (and may include both relevant and non-relevant constituents) in the rotated space. In operation, in certain embodiments, the operations can include mathematically rotating the design matrix, interrogating the rotated design matrix (using an acceptance function) to find those rotated principal components with contributions that benefit the deconvolution, and rotating back those accepted principal components to form the reduced design matrix.

In certain embodiments, a normal equations matrix (which, in certain embodiments, may be mathematically represented by matrix "$X^T X$") can be computed from the design matrix (block 225). The normal equations matrix can be interrogated by applying a predetermined acceptance function ("$A(\lambda)$") to the principal components to generate the reduced design matrix. The acceptance function can be a forced logic function of "0" and "1" (representative of rejected (excluded) values and accepted (included) values, respectively) or may be a relative or absolute function that discards the principal components having values low with respect to other components or relative to a predefined threshold (i.e., the values having the least significance) and retaining the more significant values in the reduced design matrix. The reduced matrix may be generated by rotating the design matrix and eliminating the column or columns in the rotated design matrix with the most "0"s as determined by the acceptance function.

Regression fit weighting coefficients can be computed based on accepted principal components of the rotated design matrix in the reduced design matrix to determine the presence of and/or measurement of the selected or target constituents in the unknown sample undergoing analysis (block 230). In particular embodiments, the weighting coefficients may be determined according to Equation (21) as will be discussed further below. A sequential least squares regression analysis can then be employed to restrict or restrain negative coefficients to zero until all (or substantially all) constituents of interest are non-negative (block 231). In certain embodiments, before the sequential regression analysis evaluation is performed, the reduced design matrix is combined with the composite matrix to define a first set of weighting factors.

Described differently, the signal from the unknown test sample can be projected onto the space spanned by selected principal components and the projection coefficients can be transformed back into the original space to provide a reduced design matrix for arriving at weighting coefficients. As such, the design matrix can be mapped into the rotated design matrix and the components selected to yield the reduced design matrix.

The reduced design matrix can be generated based on predetermined criteria using a shrinkage estimator. In certain embodiments, the shrinkage estimator can be based on the spectral decomposition of a matrix defined by the multiplication of the constituent matrix with the transposed constituent matrix. In certain embodiments, the shrinkage estimator can be found by projecting the constituent matrix onto the space spanned by the accepted basis set determined from the rotation of the design matrix, and shrinking the projection of the constituent matrix on the orthogonal subspace to zero. A particularly suitable shrinkage estimator is described in Equation (21).

It is noted that other shrinkage estimators may also be employed. Generally stated, a shrinkage estimator of a parameter b is any estimator $B(X)$ of the data X such that $\|E\{B(X)\}\| \leq \|b\|$. A simple example would be to take an unbiased estimator of b, say $U(X)$, and multiply by a constant smaller than 1: $B(X)=pU(X)$ where $0<p<1$. Because $U(X)$ is unbiased, by definition of unbiased, $E\{U(X)\}=b$. Then the norm of the expectation could be expressed as $\|E\{B(X)\}\|=\|E\{p\ U(X)\}\|=p\|E\{U(X)\}\|=p\|b\|<\|b\|$ since $p<1$. In the shrinkage estimator of Equation (21), shrinkage is carried out selectively, in the direction of zero for some components, and not for others.

The number of individual constituent data sets can be at least ten (10), each representing a respective one of at least ten (10) different closely correlated chemical constituents, some of the constituents having overlapping signal lines in a region of the spectrum analyzed (block 202). The number of columns in the design constituent matrix can correspond to the number of different individual constituents of interest, and, where needed, at least one additional column, which may be a matrix of variables, representing spectra contributions from at least one non-relevant variable constituent and/or noise (block 201). In operation, this additional column may not be used (i.e., "0"). The at least one non-relevant variable can be a constituent known to be in the sample but not a target interest and/or background or environmental noise, and the like.

In certain embodiments, the predetermined analysis method is NMR spectroscopy, and the composite signal represents intensity over a desired interval or region in a chemical shift spectrum (typically represented in ppm) such that intensity is the dependent variable parameter (block 212).

Figure 7:
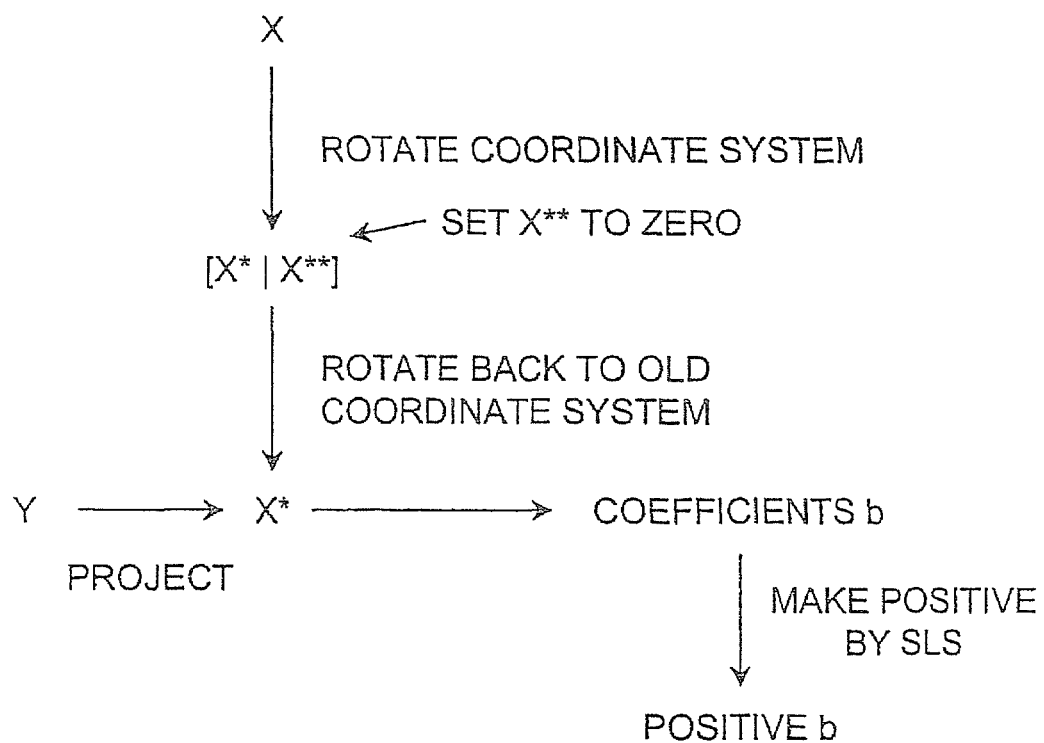
FIG. 7 is a schematic diagram of an interrogation protocol used to evaluate signal data for composite spectra having contributions from overlapping constituents according to embodiments of the present invention.

FIG. 7 is a schematic illustration of certain embodiments of the deconvolution operations used to evaluate closely correlated signal data. As shown, a design matrix "X" of constituent data comprising a plurality of individual mathematical data sets, each constituent data set including amplitude values of a respective spectrum lineshape of a selected constituent parameter over the variable space, spectrum length, or data points of interest, is obtained. The coordinate system of the design matrix is rotated to generate a rotated design matrix "Z" and, ultimately, a reduced design matrix "X*" (and a related transposed matrix "X**"). The line extending between X* and X** represents a classifier or acceptance function that determines what principal component data in X will be excluded from X*. The matrix is then rotated back to the original coordinate system, thereby generating a reduced design matrix "X*" with data from X modified by the analysis performed at the rotation of the coordinate system. The matrix of the composite spectrum lineshape data "Y" is projected onto X* and the weighting coefficients "b" calculated. A sequential least squares ("SLS") regression analysis is performed on the defined weighting coefficients to ensure that positive weighting coefficients are established. The operations may be iteratively repeated.

Figure 8:
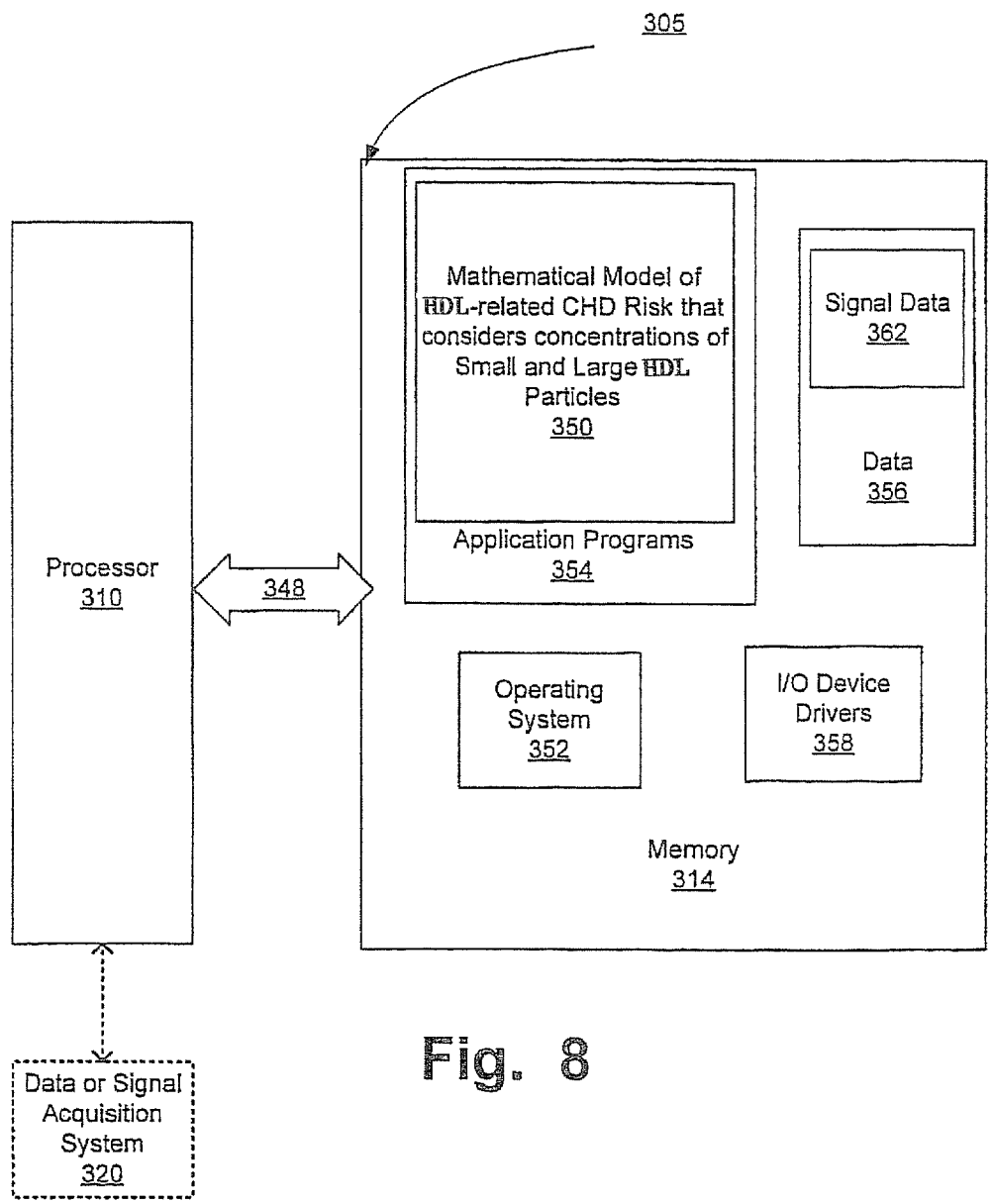
FIG. 8 is a schematic diagram of a data processing system according to embodiments of the present invention.

FIG. 8 is a block diagram of exemplary embodiments of data processing systems that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 8, the memory 314 may include several categories of software and data used in the data processing system 305: the operating system 352; the application programs 354; the input/output (I/O) device drivers 358; a Module of a Mathematical Model of HDL-related CHD Risk that considers internal concentrations of small and large HDL particles 350; and the data 356. The HDL Predictive Risk Module 350 can include a mathematical model that employs a predetermined increased weighting factor for at least one LDL particle subclass to provide a weighted risk HDL particle number that adjusts the measured values in the blood or plasma sample.

The data 356 may include signal (constituent and/or composite spectrum lineshape) data 362 which may be obtained from a data or signal acquisition system 320. As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000 or WindowsXP from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/or the image acquisition system 320. The application programs 354 are illustrative of the programs that implement the various features of the data processing system 305 and can include at least one application, which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Module 350 being an application program in FIG. 8, as will be appreciated by those of skill in the art, other configurations may also be utilized while still benefiting from the teachings of the present invention. For example, the HDL risk Model Module 350 may also be incorporated into the operating system 352, the I/O device drivers 358 or other such logical division of the data processing system 305. Thus, the present invention should not be construed as limited to the configuration of FIG. 8, which is intended to encompass any configuration capable of carrying out the operations described herein.

In certain embodiments, the Module 350 includes computer program code for providing a single risk predictor number for HDL and LDL particles as well as a total single combined risk number using the ratio of the weighted HDL and LDL risk values in a subject that can indicate whether therapy intervention is desired and/or track efficacy of a therapy using the risk predictor number as a sensitive reflection of what is occurring at the arterial wall.

For NMR derived lipoprotein measurements, the computer program code can include a sequential least squares regression analysis based on a statistical model comprising: (a) a mathematical composite matrix representing spectrum measurements of the amplitude of a composite signal of an unknown sample across "n" points in the spectrum; and (b) a design matrix including respective mathematical matrices for the amplitude of each of a plurality of individual selected constituents across "n" points in the spectrum. The shrinkage estimator and acceptance function can be used to generate optimum weighting factors "$b_{opt}$" for each constituent of interest based on the difference between the composite signal amplitude and the constituent amplitudes defined by interrogation of the values in the constituent and composite vectors. The analysis can be iteratively repeated in a sequential least squares regression model until target or selected constituents have been assigned non-negative weighting factors such that a sequential least squares statistical evaluation produces a satisfactory non-negative solution set for the target constituents.

The I/O data port can be used to transfer information between the data processing system 305 and the image scanner or acquisition system 320 or another computer system or a network (e.g., the Internet) or to other devices controlled by the processor. These components may be conventional components such as those used in many conventional data processing systems, which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 8 but is intended to encompass any configuration capable of carrying out the operations described herein.

More particularly described, in particular embodiments, a target sample to be analyzed may have a number of different selected parts or constituents or individual or groupings of selected constituents. The number of constituent parts may be noted as k. Thus, a sample undergoing analysis can include constituent parts, $P_1, \ldots, P_k$. As noted above, the number k may be at least 10, and can be between 35-40 or even larger. The sample can be analyzed on a desired suitable analytical instrument, with the amplitude of the independent variable (e.g., intensity, wavelength, retention time, current, etc., as described above) varied. The amplitude or value of the independent constituent(s) varies corresponding to the detector response of the analytical instrument and the variation can be recorded in the form of a spectrum. The spectrum or lineshape consists of amplitude measurements (that may be intensity measurements in certain embodiments) at n points. These amplitude measurements of the sample being analyzed are stored in a composite matrix, Y.

Also, each constituent part, $P_j$, j=1 to k, is separately analyzed to define a standard or reference over the same independent variable space, region, or data points as the sample undergoing analysis. Each set of the respective reference constituent spectral amplitudes (such as intensities) are stored in a matrix $X_j$, where, j=1, . . . , k, also of length n. Thus, a design constituent matrix X can be represented by:

$$X=[X_1, X_2 \ldots, X_k, Z] \quad (15)$$

where Z is a matrix of amplitude data regarding at least one additional variable that can be deconvolved from the spectral signal. For example, Z may contain data representing spectral intensities of other known or unknown constituents, the imaginary part of the spectrum of the analyte sample, (where Y contains the real part of the spectrum), noise, etc. . . . However, it is noted that Z can be a matrix, a vector, or, in certain embodiments, even null (a degenerate form of matrix with 0 columns).

In certain embodiments, Z is a matrix of size n×w, where w≥0. In certain particular embodiments, w=1. The estimated contributions of the individual components to the sample or analyte composite spectrum can be found by determining a normalized or optimal coefficient weightings $b_{opt}$ given by equation 16. The normalized weighting coefficient minimizes the values inside the brackets of the arg $\min_b$ function.

$$b_{opt} = \arg\min_b\{\|Y - Xb\|: b \geq 0\}. \quad (16)$$

These normalized weightings can be found by solving equation (16) using a shrinkage estimator to the regression problem, followed by the application of non-negative least squares to ensure that the non-negativity constraint is satisfied. The cycle is repeated until the least squares solution provides only non-negative weighting factors. The shrinkage estimator can be based on the spectral decomposition of the matrix $M = X^T X$ where $X^T$ represents a transposition of the constituent matrix X. Further, the spectral decomposition matrix M may be expressed by the following:

$$M = Q\Lambda Q^T \quad (17)$$

where Q (k+w)×(k+w) is orthogonal, and Λ (k+w)×(k+w) is a diagonal matrix comprising eigenvalues. The eigenvalue matrix Λ is sorted with the largest eigenvalue in the (1,1) element or position, the next largest value in the (2,2) element or position, and continuing left to right and top to bottom, etc. . . . , until the smallest element is placed in the (n, n) element or position. An adjustable tolerance parameter "τ" can be defined such that τ≥0. Also an acceptance or classifier function "A" can be defined such that A(λ): $\Re \to \{0, 1\}$ which indicates which component is accepted into a fitting model.

A reduced eigenvalue matrix "$\Lambda_{red}$" can be defined as:

$$\Lambda_{red} = \Lambda \mathrm{diag}(A(\Lambda_{j,j})) \quad (18)$$

The X* matrix ("reduced design matrix") described above may be identified as:

$$X^* = Q\Lambda_{red}^{1/2} \quad (19)$$

One acceptance function that has been used is:

$$A(\lambda) = \begin{cases} 1 & \text{if } \lambda > \tau\Lambda_{1,1} \\ 0 & \text{otherwise} \end{cases} \quad (20)$$

where τ has been chosen to minimize Var b while maintaining E{b}. Examples of values for τ are in the range between $10^{-6}$ and $4 \times 10^{-6}$ for cases where k is about 37, i.e., where there are about 37 constituents or parts "$P_1$—$P_{37}$". Other values may be appropriate for lesser or greater numbers of constituents. Then b can be calculated as:

$$b = Q\Lambda_{red}^{-1} Q^T X^T Y \quad (21)$$

Figure 9:
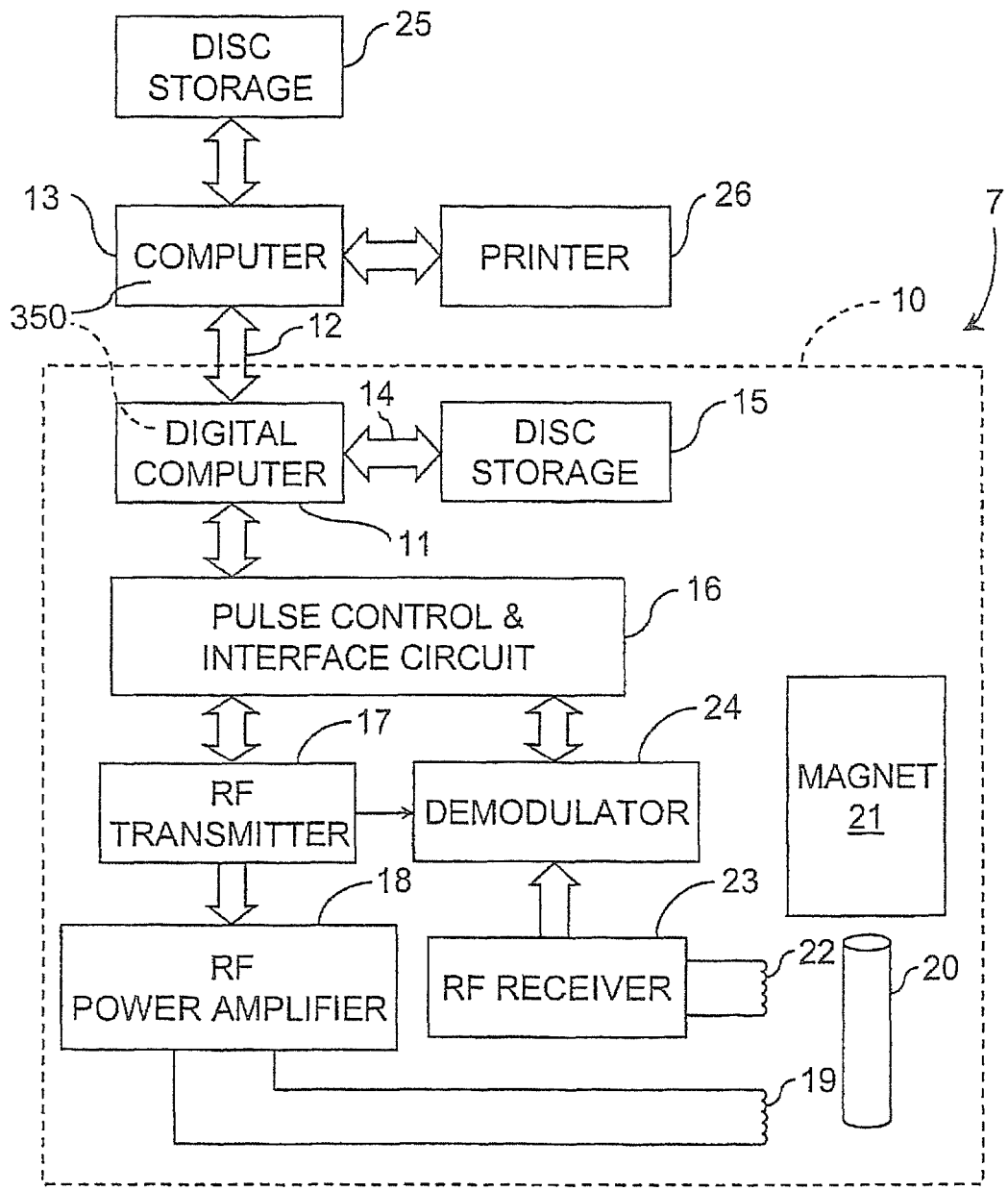
FIG. 9 is a schematic illustration of a NMR spectroscopy apparatus according to embodiments of the present invention.

Configuration of Exemplary System for Acquiring and Calculating Adjusted HDL and/or LDL Particle Subclass Concentration Measurements and/or HDL and LDL Particle Risk Numbers Referring now to FIG. 9, a system 7 for acquiring and calculating the lineshape of a selected sample is illustrated. The system 7 includes an NMR spectrometer 10 for taking NMR measurements of a sample. In one embodiment, the spectrometer 10 is configured so that the NMR measurements are conducted at 400 MHz for proton signals, in other embodiments the measurements may be carried out at 360 MHz or other suitable frequency. Other frequencies corresponding to a desired operational magnetic field strength may also be employed. Typically, a proton flow probe is installed, as is a temperature controller to maintain the sample temperature at 47+/−0.2 degrees C. Field homogeneity of the spectrometer 10 can be optimized by shimming on a sample of 99.8% $D_2O$ until the spectral linewidth of the HDO NMR signal is less than 0.6 Hz. The 90° RF excitation pulse width used for the $D_2O$ measurement is typically ca. 6-7 microseconds.

Referring again to FIG. 9, the spectrometer 10 is controlled by a digital computer 11 or other signal processing unit. The computer 11 should be capable of performing rapid Fourier transformations and may include for this purpose a hard-wired sine table and hardwired multiply and divide circuit. It may also include a data link 12 to an external personal computer 13, and a direct-memory-access channel 14 which connects to a hard disc unit 15.

The digital computer 11 may also include a set of analog-to-digital converters, digital-to-analog converters and slow device I/O ports which connect through a pulse control and interface circuit 16 to the operating elements of the spectrometer. These elements include an RF transmitter 17 which produces an RF excitation pulse of the duration, frequency and magnitude directed by the digital computer 11, and an RF power amplifier 18 which amplifies the pulse and couples it to the RF transmit coil 19 that surrounds sample cell 20. The NMR signal produced by the excited sample in the presence of a 9.4 Tesla polarizing magnetic field produced by superconducting magnet 21 is received by a coil 22 and applied to an RF receiver 23. The amplified and filtered NMR signal is demodulated at 24 and the resulting quadrature signals are applied to the interface circuit 16 where they are digitized and input through the digital computer 11 to a file in the disc storage 15. The module 350 (FIG. 8) can be located in the digital computer 11 and/or in a secondary computer that may be on-site or remote. Additional automated clinical NMR analyzer systems suitable for analyzing biospecimen are described in co-pending, co-assigned U.S. patent application Ser. No. 11/093,596, the contents of which are hereby incorporated by reference as if recited in full herein.

After the NMR data are acquired from the sample in the measurement cell 20, processing by the computer 11 produces another file that can, as desired, be stored in the disc storage 15. This second file is a digital representation of the chemical shift spectrum and it is subsequently read out to the computer 13 for storage in its disc storage 25. Under the direction of a program stored in its memory, the computer 13, which may be personal, laptop, desktop, or other computer, processes the chemical shift spectrum in accordance with the teachings of the present invention to print a report, which is output to a printer 26 or electronically stored and relayed to a desired email address or URL. Those skilled in this art will recognize that other output devices, such as a computer display screen, may also be employed for the display of results.

It should be apparent to those skilled in the art that the functions performed by the computer 13 and its separate disc storage 25 may also be incorporated into the functions performed by the spectrometer's digital computer 11. In such case, the printer 26 may be connected directly to the digital computer 11. Other interfaces and output devices may also be employed, as are well-known to those skilled in this art.

The invention will now be described in more detail in the following non-limiting examples.

EXAMPLES

Exemplary weighting factors for LDL subclasses (Examples 1 and 2) and HDL subclasses (Example 3) were calculated using data from different studies with different coronary disease outcomes. Example 1 uses data on relations of large and small LDL particle numbers with carotid atherosclerosis as assessed on a per particle basis. Example 2 uses data on relations of IDL, large LDL, and small LDL particle numbers with incident CHD events (nonfatal myocardial infarction and CHD death) as assessed on a per particle basis. Example 3 uses data on relations of small, large and medium HDL particle numbers with carotid atherosclerosis as assessed on a per particle basis.

Example 1

Shown in the table are the relations of large and small LDL particle numbers with carotid atherosclerosis as assessed on a per particle basis. TABLE 2 is an example of LDL subclass weights using data presented in Mora et al., *Both Large and Small LDL Particle Concentrations are Independently Associated with Carotid Atherosclerosis in the Multi-Ethnic Study of Atherosclerosis (MESA)*, Abstract presented at 2005 Scientific Sessions of the American Heart Association, Dallas, Tex., Circulation. 2005; 112: II-802.

TABLE 2

Exemplary LDL subclass weighting for Carotid Atherosclerosis

| | Δ IMT (per 100 nmol/L) | LDL subclass weighting |
|---|---|---|
| Large LDL-P | 17.5 microns | 1.5 |
| Small LDL-P | 11.8 microns | 1.0 |

Data are from a linear regression model including both large and small LDL-P, adjusted for age, race, sex, hypertension, and smoking.

Shown in TABLE 2 are exemplary relations of large and small LDL particle numbers with carotid atherosclerosis as assessed on a per particle basis based on the MESA study. Subjects were 5,354 apparently healthy individuals enrolled in the Multi-Ethnic Study of Atherosclerosis (MESA) who were not taking lipid-lowering medication. Data show the change (increase) in carotid intima-media thickness (IMT) per 100 nmol/L increment in the concentration of large and small LDL-P. The ratio of Δ IMT for large LDL-P/small LDL-P is about 1.5, which gives a weighting factor for large LDL-P relative to small LDL-P.

It is contemplated that a third LDL subclass (IDL) can be included in the risk model and a different LDL subclass weighting can be used for the IDL contribution. IDL-P may have a weighting factor, which may be higher than the large LDL-P weight, such as between about 5-6 relative to small LDL-P.

Example 2

Shown in TABLE 3 are the relationships of IDL and large and small LDL particle numbers with incident CHD events (nonfatal myocardial infarction and CHD death) as assessed on a per particle basis. The data was derived from results presented in Otvos et al., *Low-Density Lipoprotein and High-Density Lipoprotein Particle Subclasses Predict Coronary Events and Are Favorably Changed by Gemfibrozil Therapy in the Veterans Affairs High-Density Lipoprotein Intervention Trial*, Circulation. 2006; 113; 1556-1563; originally published online Mar. 13, 2006.

TABLE 3

Exemplary LDL subclass weighting for incident CHD Events

| | 1 SD | Odds Ratio (per 1 SD) | Beta coefficient (per 100 nmol/L) | LDL subclass weighting |
|---|---|---|---|---|
| IDL-P | 28 nmol/L | 1.13 | 0.436 | 5.7 |
| Large LDL-P | 250 nmol/L | 1.34 | 0.117 | 1.5 |
| Small LDL-P | 450 nmol/L | 1.41 | 0.076 | 1.0 |

Data are from a logistic regression model including LDL and HDL subclasses in the same model, adjusted for treatment group, age, hypertension, smoking, body mass index, and diabetes.

Subjects were men (364 cases, 697 controls) with existing coronary disease enrolled in the Veterans Affairs HDL Intervention Trial (VA-HIT). Data show the odds ratios for a new CHD event associated with a 1 SD increment in the on-trial concentration of each LDL subclass. The corresponding beta coefficients show the relationships of each subclass to CHD events on a per particle basis. The ratios of the beta coefficients for IDL-P and large LDL-P relative to small LDL-P give the weighting factors for IDL-P and large LDL-P relative to small LDL-P.

The beta coefficients can be calculated according to the mathematical expression:

beta coeff=ln OR/1SD(100).

Example 3

Table 4 below contains data from MESA relating the different HDL subclasses to carotid IMT and shows the resulting weighting factors. The HDL risk factor can be provided as a discrete risk factor and can be used to generate a parameter called $R_{HDL}$ or Risk $_{HDL}$ (or suitable identifier) to be calculated like $R_{LDL}$. The $R_{HDL}$ could also be called the "Good Particle Index" and the $R_{LDL}$ could be called the "Bad Particle Index". A combined parameter (called the Lipoprotein Particle Index or the like) using the ratio of Bad/Good Particle Indexes could be reported similar to the TC/HDL-C or LDL-C/HDL-C ratio.

TABLE 4

Exemplary HDL subclass weights

| | 1 SD | Δ IMT (per 1 SD) | Δ IMT (per 1 μmol/L) | HDL subclass weighting |
|---|---|---|---|---|
| Large HDL-P | 4.0 μmol/L | −25.1 microns | −6.3 microns | 2.2 |
| Medium HDL-P | 4.2 μmol/L | −16.6 microns | −3.9 microns | 1.4 |
| Small HDL-P | 4.6 μmol/L | −13.2 microns | −2.9 microns | 1.0 |

It is contemplated that additional studies may further optimize the weighting factors.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of determining a subject's risk of having and/or developing coronary heart disease, comprising:
   conducting Nuclear Magnetic Resonance to obtain concentration measurements of small and large High Density Lipoprotein subclass particles from a single in vitro blood plasma or serum sample of a subject; and
   programmatically numerically adjusting at least one of the obtained small and large High Density Lipoprotein subclass particle concentration measurements of the single in vitro blood plasma and/or serum sample based on a predetermined mathematical model with at least one weighting factor that is multiplied to increase or decrease the small and/or large High Density Lipoprotein subclass particle concentration measurements, wherein the at least one weighting factor reflects predicted CHD risk for the weighted High Density Lipoprotein subclass, to yield a High Density Lipoprotein risk number that can be greater than a summation of an actual, unadjusted total High Density Lipoprotein particle concentration measurement, to thereby determine the subject's High Density Lipoprotein based risk of coronary heart disease.

2. A method according to claim 1, further comprising conducting Nuclear Magnetic Resonance to obtain concentration measurements of medium High Density Lipoprotein particles in the sample, and wherein the adjusting step is carried out to electronically adjust at least two of the small subclass particle measurements, the large High Density Lipoprotein subclass particle measurement and the medium High Density Lipoprotein particle measurement and calculating the High Density Lipoprotein risk number based on the at least two adjusted particle concentration measurements.

3. The method of claim 1, further comprising electronically generating a report with actual High Density Lipoprotein particle subclass concentrations and the High Density Lipoprotein risk number.

4. A method for determining a subject's risk of coronary heart disease, comprising:
   conducting Nuclear Magnetic Resonance to obtain concentration measurements of small and large High Density Lipoprotein subclass particles in a biosample of interest;
   multiplying a weighting factor by at least one of the measured large and small High Density Lipoprotein particle concentrations; and
   calculating a High Density Lipoprotein risk number using the weighted High Density Lipoprotein particle concentration(s), wherein the High Density Lipoprotein risk number is a discrete parameter separate from actual High Density Lipoprotein subclass particle concentrations and that is different from a summation of the obtained actual small and large High Density Lipoprotein particle concentration measurements,
   wherein the obtaining, multiplying and calculating steps are carried out using at least one processor.

5. A method according to claim 4, wherein the High Density Lipoprotein risk number comprises a weighted large High Density Lipoprotein particle concentration summed with an actual unadjusted small High Density Lipoprotein particle concentration.

6. A method according to claim 5, wherein the obtaining step comprises:
   deconvolving at least one Nuclear Magnetic Resonance spectroscopic signal of the biosample to calculate the small and large High Density Lipoprotein particle subclass concentration measurements.

7. A method according to claim 6, wherein the obtaining step obtains a concentration measure of medium High Density Lipoprotein particles, and wherein the multiplying at least one weighting factor step is carried out to increase the medium High Density Lipoprotein particle measurement and the large High Density Lipoprotein particle measurement relative to the small High Density Lipoprotein particle measurement.

8. A method according to claim 7, wherein the biosample is an in vitro blood plasma and/or serum sample, and wherein the multiplying step is carried out to increase the medium High Density Lipoprotein particle measurement more than the large High Density Lipoprotein particle measurement.

9. A method according to claim 4, wherein the multiplying step is carried out to apply an increased weight to the large High Density Lipoprotein subclass concentration measurement relative to the small High Density Lipoprotein subclass concentration to calculate the High Density Lipoprotein risk number.

10. A computer program product for adjusting measured in vitro concentrations of High Density Lipoprotein particles to assess coronary heart disease risk, the computer program product comprising:
    a non-transitory computer readable storage medium having embodied in said medium computer readable program code that:
    (i) deconvolutes at least one Nuclear Magnetic Resonance signal of a patient biosample into measured concentrations of small and large High Density Lipoprotein particle subclasses; and
    (ii) adjusts concentration measurements of at least one of small and large High Density Lipoprotein particle subclasses of a biosample to generate a High Density Lipoprotein risk number to reflect a subject's risk of having or developing coronary heart disease, wherein the High Density Lipoprotein risk number is calculated based on a defined mathematical model to yield a numerical High Density Lipoprotein risk number that is different from a summation of the obtained actual small and large High Density Lipoprotein particle concentration measurements.

11. A computer program product according to claim 10, wherein the mathematical model is configured to increase the measured large High Density Lipoprotein particle concentration measurement relative to the small High Density Lipoprotein particle concentration to define the High Density Lipoprotein risk number.

12. A computer program product according to claim 11, wherein the mathematical model is configured to multiply a first weighting factor by the concentration measurement of small High Density Lipoprotein particles and multiply a second different weighting factor by the concentration measurement of large High Density Lipoprotein particles and sum the weighted small and large High Density Lipoprotein particles to generate the High Density Lipoprotein risk number.

13. A computer program product according to claim 12, wherein the computer readable program code of the mathematical model is configured to increase the actual large High Density Lipoprotein particle concentration measurement relative to the actual small High Density Lipoprotein particle concentration measurement.

14. A computer program product according to claim 10, wherein the computer readable program code that adjusts at least one of the measured small and large High Density Lipoprotein particle concentrations is configured to adjust at least two of small High Density Lipoprotein particle concentration, large High Density Lipoprotein particle concentration and medium High Density Lipoprotein particle concentration such that both the large High Density Lipoprotein and the medium High Density Lipoprotein particle measurements are increased relative to the small High Density Lipoprotein subclass measurement to generate the High Density Lipoprotein risk number.

15. A computer program product according to claim 14, further comprising computer readable program code that defines the High Density Lipoprotein risk number using a summation of the adjusted small and/or large High Density Lipoprotein particle concentrations and scales the summation to thereby define a corresponding High Density Lipoprotein-based coronary heart disease risk.

16. A computer program product according to claim 10, further comprising computer readable program code that calculates the High Density Lipoprotein particle risk number in units of concentration.

17. A computer program product according to claim 10, wherein the computer readable program code that adjusts the High Density Lipoprotein particle measurement(s) is configured to generate different weighting factors for small and large High Density Lipoprotein particles to predict coronary heart disease risk.

18. A computer program product according to claim 10, wherein the computer readable program code is configured to increase the large High Density Lipoprotein particle measurement relative to the small High Density Lipoprotein particle measurement to adjust the actual measurements from the in vitro blood plasma or serum sample.

19. A system for obtaining data regarding lipoprotein constituents in a subject, comprising:
  a Nuclear Magnetic Resonance spectrometer for acquiring at least one Nuclear Magnetic Resonance spectrum of an in vitro blood, plasma or serum sample from a subject; and
  at least one processor in communication with the Nuclear Magnetic Resonance spectrometer, the at least one processor configured to:
  determine concentrations of small and large High Density Lipoprotein particle subclasses in the sample; and
  multiply at least one weighting factor by at least one of the determined small and large High Density Lipoprotein particle concentrations of the sample and sum weighted and unweighted concentrations to yield a numerical High Density Lipoprotein risk number for the sample that is different from a summation of the obtained actual small and large High Density Lipoprotein particle concentration measurements to determine a subject's risk of developing or having coronary heart disease.

20. A system according to claim 19, wherein the at least one Nuclear Magnetic Resonance spectrum is a composite spectrum, the processor further configured to execute computer program code defining a plurality of individual Nuclear Magnetic Resonance constituent spectra, each associated with a selected reference lipoprotein constituent signal lineshape, each constituent spectrum having associated spectra that contribute to the composite Nuclear Magnetic Resonance spectrum of the blood plasma or serum sample.

21. A system according to claim 19, wherein the at least one processor is configured to increase the actual measured large High Density Lipoprotein particle concentration relative to the actual small High Density Lipoprotein particle concentration of the respective single samples.

22. A system according to claim 21, wherein the at least one processor is configured to define a first weighting factor that is multiplied by the small High Density Lipoprotein particle concentration and a second different weighting factor that is multiplied by the large High Density Lipoprotein particle concentration, wherein the second weighting factor is larger than the first weighting factor.

23. A system according to claim 19, wherein the at least one processor is configured to multiply at least one weighting factor to at least one of the determined small and large High Density Lipoprotein particle concentrations of the sample to increase the measured concentration of medium High Density Lipoprotein particles and the measured concentration of large High Density Lipoprotein particles but not to the small High Density Lipoprotein particle measurement to determine coronary heart disease risk.

24. A system according to claim 23, wherein the at least one processor is configured to generate a High Density Lipoprotein risk number using the adjusted High Density Lipoprotein particle concentrations.

25. A method of evaluating a person's risk of having or developing coronary heart disease, comprising:
  electronically calculating a High Density Lipoprotein risk number for a person using a summation of at least two of small, medium and large High Density Lipoprotein particle concentration values of a biosample from the person, wherein at least one of the concentration values for the summation for the sample is electronically increased, using a processor, relative to the measured small High Density Lipoprotein particle concentration value using a predefined weighting factor, wherein the High Density Lipoprotein risk number can have a concentration value that is greater than a total actual High Density Lipoprotein subclass concentration measurement.

26. A method according to claim 25, further comprising electronically, using a processor, defining a risk of developing or having coronary heart disease associated with the High Density Lipoprotein risk number.

27. A method according to claim 25, further comprising using a processor to mathematically scale the calculated risk number.

28. A method according to claim 25, further comprising using a processor to increase both the medium High Density Lipoprotein and large High Density Lipoprotein particle concentration values relative to actual small High Density Lipoprotein particle concentration value and summing these increased values with the actual small High Density Lipoprotein particle concentration measurement value to generate the High Density Lipoprotein risk number.

29. A method according to claim 28, further comprising using a processor to calculate a Low Density Lipoprotein risk number using at least two of small, medium and large Low Density Lipoprotein particle concentration values, wherein at least one of the concentration values is increased using a defined weighting factor relative to the measured small Low Density Lipoprotein particle concentration value.

30. A method according to claim 29, further comprising using a processor to calculate a lipoprotein particle index from a ratio of the Low Density Lipoprotein risk number to the High Density Lipoprotein risk number.

31. A method according to claim 30, further comprising using a processor to generate a patient-specific report presenting the lipoprotein particle index, the Low Density Lipoprotein risk number and the High Density Lipoprotein risk number.

32. A method according to claim 25, wherein the calculating step is carried out using at least one processor.

33. A method of assessing coronary heart disease risk in a patient, comprising:

generating a single risk predictor variable using a ratio of a Low Density Lipoprotein particle number as a numerator and a High Density Lipoprotein particle number as a denominator, wherein the generating step is carried out using at least one processor, and wherein the Low Density Lipoprotein and High Density Lipoprotein particle numbers are calculated using at least one predefined weighting factor that is multiplied by an actual concentration measurement of at least one subclass of respective Low Density Lipoprotein and High Density Lipoprotein particle subclasses, wherein the multiplied concentration of at least one subclass of respective Low Density Lipoprotein and High Density Lipoprotein particle subclasses increases or decreases actual concentrations of the Low Density Lipoprotein particle number and the High Density Lipoprotein particle number and are different from a summation of total Low Density Lipoprotein particle number and total High Density Lipoprotein particle number.

* * * * *